United States Patent
Young et al.

(10) Patent No.: US 7,301,006 B2
(45) Date of Patent: Nov. 27, 2007

(54) METHODS AND MATERIALS FOR THE SYNTHESIS OF MODIFIED PEPTIDES

(75) Inventors: Travis G. Young, Portland, OR (US); Laura L. Kiessling, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 569 days.

(21) Appl. No.: 10/622,078

(22) Filed: Jul. 16, 2003

(65) Prior Publication Data

US 2004/0063918 A1    Apr. 1, 2004

Related U.S. Application Data

(60) Provisional application No. 60/396,832, filed on Jul. 16, 2002.

(51) Int. Cl.
C07C 247/04 (2006.01)
C07C 247/06 (2006.01)
C07C 247/18 (2006.01)
C07K 1/06 (2006.01)

(52) U.S. Cl. ............... 530/336; 552/5; 552/8; 552/12

(58) Field of Classification Search ............ None
See application file for complete search history.

(56) References Cited

U.S. PATENT DOCUMENTS 4,369,137 A * 1/1983 Heavner ............ 530/330

(Continued)

OTHER PUBLICATIONS

Crimmin et al. Synthesis Of Phenolically Linked Cyclic Peptides. Tetrahedron Letters. 1990, vol. 31, No. 14, pp. 2021-2024.*

(Continued)

Primary Examiner—Jeffrey Edwin Russel
(74) Attorney, Agent, or Firm—Greenlee Winner and Sullivan, PC

(57) ABSTRACT

Methods and protected amino acids useful as building blocks (protected monomers) for the synthesis of peptides and proteins that are selectively modified at one or more side-chain hydroxyl groups. Azide-bearing protecting groups allow the selective deprotection of side-chain hydroxyl groups of amino acids after synthesis of a peptide. Reaction conditions for removal of the azide-bearing protecting group can be selected which are substantially orthogonal to those that will remove α-amino protecting groups typically employed in peptide synthesis, such that hydroxyl groups protected with the azide-bearing protecting group remain protected during synthesis of the peptide chain. Various protecting groups which are readily available can be used for protecting potentially reactive side chain groups of amino acids in the peptide or protein to be modified. Preferred side-chain protecting groups are chemically distinguishable from the azide-bearing protecting group and substantially orthogonal reaction conditions can be selected such that side-chain protection of other amino acids is maintained when the azide-bearing protecting group is removed. The use of the azide-bearing protecting group of this invention for one or more hydroxy amino acids during peptide synthesis allows the selective unmasking of those azide-protected side-chain hydroxyl groups and selective modification of the hydroxyl groups that are selectively unmasked. The methods and materials herein are particularly used in synthesis of sulfated, phosphorylated and glycosylated peptides and proteins. Kits and methods of synthesizing a modified peptide or protein using the kits are also provided.

46 Claims, 4 Drawing Sheets

Overview of sulfated peptide synthesis.

U.S. PATENT DOCUMENTS 5,858,670 A * 1/1999 Lam et al. .................... 435/6
6,500,924 B1 * 12/2002 Brooks et al. ............. 530/350

OTHER PUBLICATIONS

Kusumoto et al. (1986) "4-Azidobutyryl Group for Temporary Protection of Hydroxyl Functions," Bull. Chem. Soc. Jpn. 59:1296-1298.

Loubinoux et al. (1991) "Protection Des Acides Par Les Groupments ABz Utilisation En Synthese Peptidique," Tetrahedron 47(2):239-248.

Loubinoux et al. (1988) "Protection of Phenols Via the Azidomethylene Group: Application in the Synthesis of Unusable Phenolic Compounds," Tetrahedron 44(19):6055-6064.

Loubinoux et al. (1991) "Protection of Amines with the 4-Azidomethylenoxybenzyloxycarbonyl Group," Tetrahedron Lett. 32(3):351-354.

Loubinoux et al. (1989) "Reactivity of New Precursors of Quinone Methides," Tetrahedron Lett. 30:1939-1942.

Lindquist et al. (2001) "Improved Solid-Phase Peptide Synthesis Method Utilizing Alpha-Azide-Protected Amino Acids," Org. Lett. 3(5):781-783.

Maiti et al. (1986) "Facile Conversions of Azides to Amines," Tetrahedron Lett. 27(13):1423-1424.

Malkinson et al. (2000) "Synthesis of C-Terminal Glycopeptides from Resin-Bound Glycosyl Azides via a Modified Staudinger Reaction," J. Org. Chem. 65:5249-5252.

Meldal et al. (1997) "Azido Acids in a Novel Method of Solid-Phase Peptide Synthesis," Tetrahedron Lett. 38 (14):2531-2534.

Patek, M. (1993) "Multistep Deprotection for Pepide Chemistry," Int. J. Peptide Protein Res. 42:97-117.

Scriven et al. (1988) "Azides: Their Preparation and Synthetic Uses," Chem. Rev. 88:297-368.

Young et al. (2002) "A Strategy for the Synthesis of Sulfated Peptides," Angew Chem. Int Ed. 41(18):3449-3451.

Young, T. (2001) "A Strategy for the Synthesis of Sulfated Peptides," PhD Thesis, University of Wisconsin-Madison.

* cited by examiner

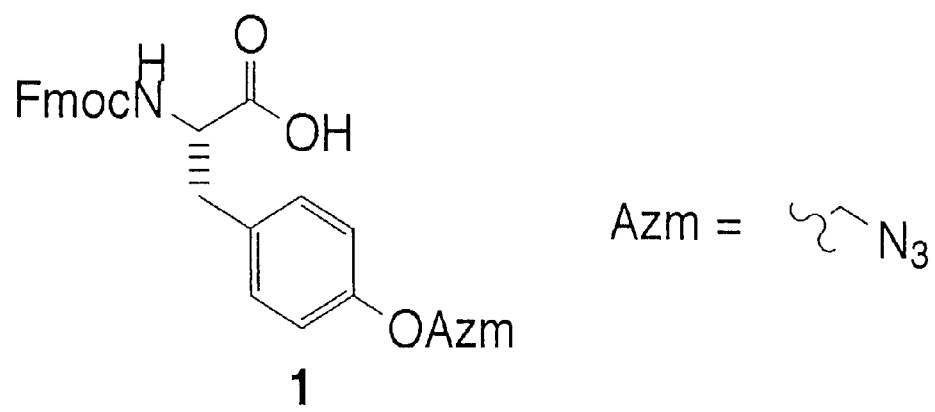
Figure 1. Target protected tyrosine building block

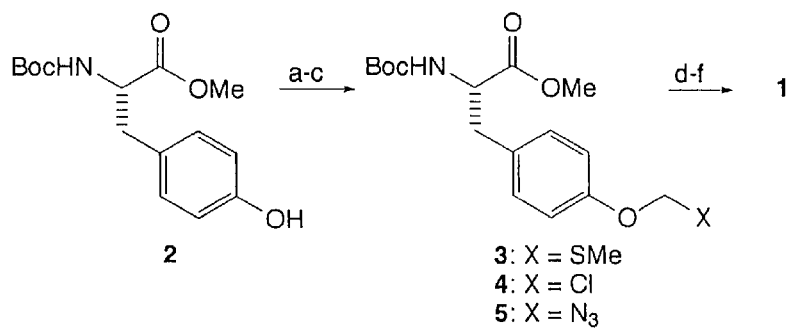
Figure 2. Scheme for the synthesis of target 1. Conditions: (a) KO*t*-Bu, NaI, CH$_3$SCH$_2$Cl, DMF, 82%; (b) NCS, TMSCl, CH$_2$Cl$_2$; (c) NaN$_3$, DMF, H$_2$O, 87% (over 2 steps); (d) TMSOTf, CH$_2$Cl$_2$; (e) FmocOSu, Et$_3$N, THF, 84% (over 2 steps); (f) LiOH-H$_2$O, THF-H$_2$O, 0 °C, 88%.

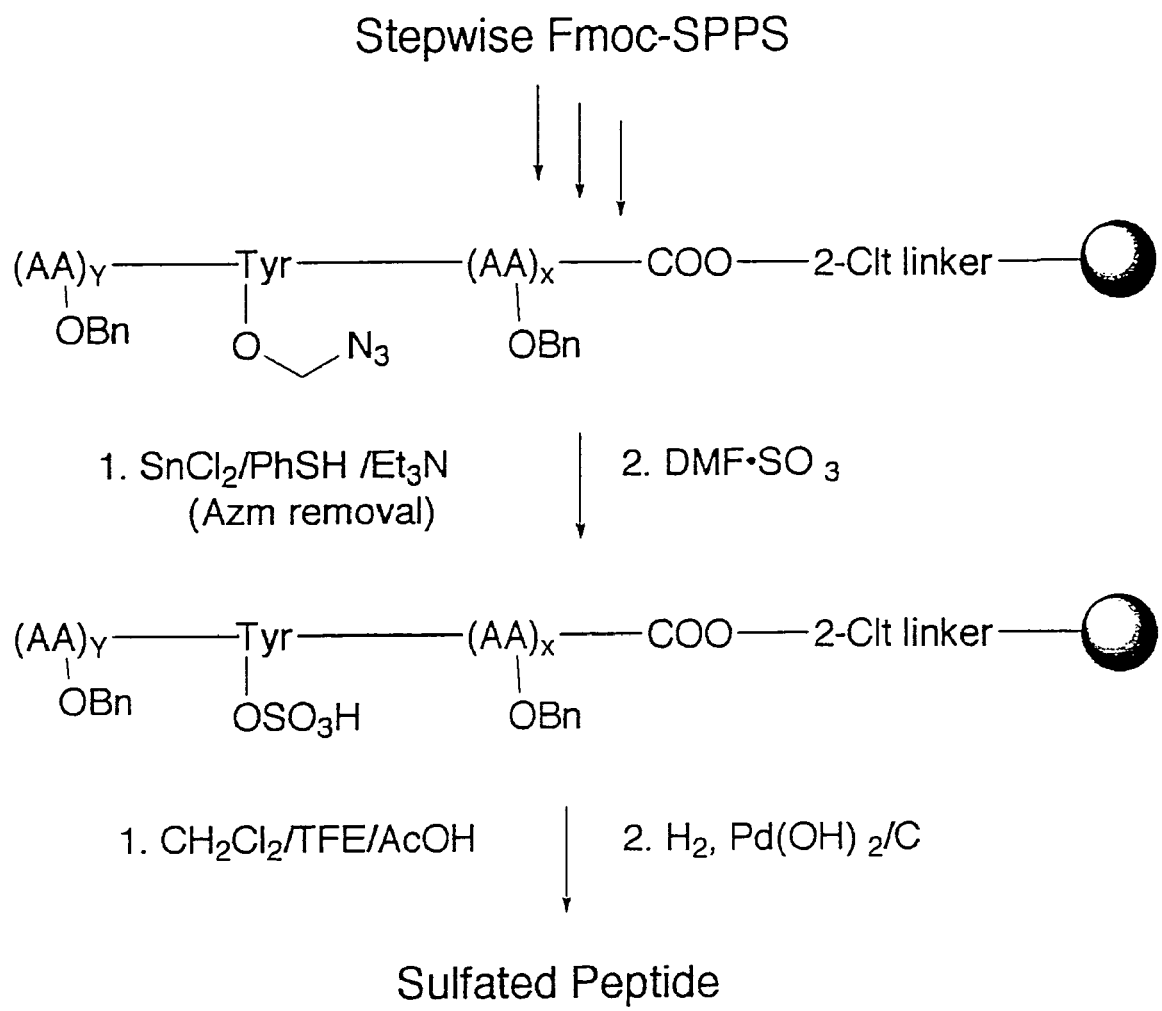
Figure 3. Overview of sulfated peptide synthesis.

SEQUENCE LISTING

```
<160> NUMBER OF SEQ ID NOS: 5

<210> SEQ ID NO 1
<211> LENGTH: 8
<212> TYPE: PRT
<213> ORGANISM: Rattus norvegicus

<400> SEQUENCE: 1

Asp Tyr Met Gly Trp Met Asp Phe
1               5

<210> SEQ ID NO 2
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (1)..(8)
<223> OTHER INFORMATION: Y at positions 1, 3, and 6 are sulfated.

<400> SEQUENCE: 2

Tyr Glu Tyr Leu Asp Tyr Asp Phe
1               5

<210> SEQ ID NO 3
```

```
                             -continued

<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (1)..(8)
<223> OTHER INFORMATION: Y at positions 1 and 6 are hydroxylated; Y at
      position 3 is sulfated.

<400> SEQUENCE: 3

Tyr Glu Tyr Leu Asp Tyr Asp Phe
1               5

<210> SEQ ID NO 4
<211> LENGTH: 8
<212> TYPE: PRT
<213> ORGANISM: Artificial
<220> FEATURE:
<223> OTHER INFORMATION: Synthetic peptide

<400> SEQUENCE: 4

Tyr Glu Tyr Leu Asp Tyr Asp Phe
1               5

<210> SEQ ID NO 5
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (1)..(7)
<223> OTHER INFORMATION: Y at position 2 is sulfated.

<400> SEQUENCE: 5

Glu Tyr Leu Asp Tyr Asp Phe
1               5
```

METHODS AND MATERIALS FOR THE SYNTHESIS OF MODIFIED PEPTIDES

CROSS-REFERENCE TO RELATED APPLICATIONS

This application takes priority under 35 U.S.C. §119(e) to U.S. provisional application 60/396,832, filed Jul. 16, 2002, which is incorporated by reference herein in its entirety.

STATEMENT REGARDING U.S. GOVERNMENT SUPPORT

This research was supported under a United States Government grant through the National Institutes of Health grant number GM49975. The United States Government has certain rights in this invention.

BACKGROUND OF THE INVENTION

This invention relates generally to methods for the synthesis of modified peptides and proteins, particularly to peptides and proteins that are selectively modified by sulfation, phosphorylation and/or glycosylation, using a new protecting group strategy.

Study of the biological functions and molecular interactions of side-chain modified peptides and proteins has generally been hampered by lack of access to the necessary quantities of selectively modified proteins and peptides. Of particular interest are peptides and proteins in which the side-chains of hydroxylated amino acids, including tyrosine, serine and threonine are modified to carry a sulfate group, a phosphate group or saccharides.

The present invention employs hydroxyl protecting groups having an azide moiety. The azide bearing protecting groups are generally stable to deprotection under acidic and basic conditions. An exemplary azide-bearing protecting group is the azidomethylene group ($-CH_2-N_3$). Loubinoux B. et al. (1988) Tetrahedron 44:6055-6064 and Loubinoux B. et al. (1989) Tetrahedron Lett. 30:1939-1942 report the use of the azidomethylene protecting group in the preparation of unstable phenols. The azidomethylene group is used to protect the hydroxyl group of the phenol and is reported to be stable under mild acidic, basic, nucleophilic and weakly reducing conditions. The azidomethylene group is also reported to be stable in the presence of $KMnO_4$, but to be removed by reducing agents such as $LiAlH_4$. For many of the syntheses reported, the azidomethylene protecting group was removed to regenerate the phenol under reducing conditions by treatment with hydrogen in the presence of palladium on carbon at 25° C. at atmospheric pressure. The azidomethylene group was also reported to be removed by treatment with triphenylphosphine then water in THF at 25° C. Additionally, it was reported that very mild conditions using stannous chloride as described by Maiti, S. N. et al. (1986) Tetrahedron Lett. 27:1423 were required to avoid polymerization of derivatized phenols.

Loubinoux, B. and Gerardin, P. (1991) Tetrahedron 47:239-248 (see also Patek, M. (1993) Int'l J. Peptide Protein Research 42:97-117) report the use of azidomethoxybenzyl esters (Abz) as protecting groups for the carboxy group in peptide synthesis using Boc α-amino protection strategy. Loubinoux B. and Gerardin P. (1991) Tetrahedron Lett. 32:351-354 also report the use of the Abz group for the protection of amines.

The subject matter of this invention has at least in part described in Young, T. (2001) "A Strategy for the Synthesis of Sulfated Peptides" Ph.D. Thesis University of Wisconsin (Madison) Volume 62/07-B Dissertation Abstracts International, as well as in Young, T.; Kiessling, L. L. *A Strategy for the Synthesis of Sulfated Peptides* 2002, Angewandte Chem. Int. Ed. 41, 3449-3451.

This invention relates in certain embodiments to phosphopeptide and sulfopeptide synthesis. Various methods for the synthesis of phosphopeptides and sulfopeptides have been reported.

Phosphopeptides can be synthesized in general by two strategies: a building block approach and a global phosphorylation method (Perich, J. W. (1991) Synthesis of O-Phospho serine-Containing and O-Phosphothreonine-Containing Peptides, Methods in Enzymology 201, 225-233; Perich, J. W. (1991) Synthesis of O-Phosphotyrosine-Containing Peptides, Methods in Enzymology 201, 234-245; Perich, J. W. (1997) Synthesis of phosphopeptides using modern chemical approaches, In Solid-Phase Peptide Synthesis, Methods in Enzymology 289, pp. 245-266). The building block approach involves the stepwise incorporation of protected phosphoamino acids at the peptide synthesis stage. Incorporation of Fmoc-phospho tyrosine without phosphate ester protection (Ottinger, E. A. (1996) Peptide Research 9, 223) in Fmoc based peptide synthesis has been reported. In addition, the use of the methyl (Valerio, R. M., Perich, J. W., Kitas, E. A., Alewood, P. F., and Johns, R. B. (1989) Synthesis of O-Phosphotyrosine-Containing Peptides 2, Solution-Phase Synthesis of Asn-Glu-Ptyr-Thr-Ala Through Methyl Phosphate Protection, Australian Journal of Chemistry 42, 1519-1525), benzyl (Kitas, E. A., Knorr, R., Trzeciak, A., and Bannwarth, W. (1991) Alternative Strategies for the Fmoc Solid-Phase Synthesis of O-4-Phospho-L-Tyrosine-Containing Peptides, Helvetica Chimica Acta 74, 1314-1328; Kitas, E. A., Wade, J. D., Johns, R. B., Perich, J. W., and Tregear, G. W. (1991) Preparation and Use of N-Alpha-Fluorenylmethoxycarbonyl O-Dibenzylphosphono-L-Tyrosine in Continuous-Flow Solid-Phase Peptide-Synthesis, Journal of the Chemical Society-Chemical Communications, 338-339), allyl and t-butyl (Perich, J. W., and Reynolds, E. C. (1991) Fmoc Solid-Phase Synthesis of Tyr(P)-Containing Peptides Through Tert-Butyl Phosphate Protection, International Journal of Peptide and Protein Research 37, 572-575) phosphate esters in Fmoc synthesis have been reported. Peptide synthesis with FmocTyr ($PO_3H_2$) has been reported for the introduction of phosphotyrosine (Ottinger, E. A., Shekels, L. L., Bernlohr, D. A., and Barany, G. (1993) Synthesis of Phosphotyrosine-Containing Peptides and Their Use As Substrates For Protein-Tyrosine Phosphatases, Biochemistry 32, 4354-4361). This amino acid derivative appears to be suitable for the synthesis of small (less than 10 residues) phosphopeptides in good yield by standard Fmoc-SPPS techniques. However, couplings to form amide bonds using this derivative tend to be sluggish. Peptides with adjacent phosphotyrosine residues also tend to undergo condensation, forming a pyrophosphate derivative (Garcia Echeverria, C. (1995) Letters in Peptide Science 2, 93; Ottinger, E. A. (1996) Peptide Research 9, 223). In recent years, the use of the monophosphate protected species FmocTyr[PO(OBzl)OH] has gained prominence (White, P., and Beythien, J. (1996) In Innovations and Perspectives in Solid Phase Synthesis & Combinatorial Libraries, 4th International Symposium, R. Epton, ed. (Birmingham: Mayflower Scientific Ltd.), pp. 557). This tyrosine derivative exhibits improved reactivity and solubility properties relative to FmocTyr($PO_3H_2$). Phosphoserine derivatives can undergo p-elimination to the corresponding dehydroalanine species on treatment with piperidine in the standard Fmoc removal protocol. This elimination is rapid if the phosphate is bis-protected (Lacombe, J. M., Andriamanampisoa, F., and Pavia, A. A. (1990) Solid-Phase Synthesis of Peptides Containing Phosphoserine Using Phosphate tert-Butyl Protecting Group, International Journal of Peptide and Protein Research 36, 275-280). This problem can be largely mitigated through the use of the monoprotected phosphoserine derivative FmocSer [PO(OBzl)OH] (Wakamiya, T., Saruta, K., Yasuoka, J., and Kusumoto, S. (1994) An Efficient Procedure For Solid-Phase Synthesis of Phosphopeptides by the Fmoc Strategy, Chemistry Letters, 1099-1102). This derivative and the analogous threonine derivative have been applied to the synthesis of a range of peptides (White and Beythien, 1996). It has been noted with these derivatives too, that coupling of consecutive residues is sluggish. Stepwise incorporation of phosphoamino acid derivatives is not possible with Boc-based peptide synthesis, since the iterative Boc cleavage conditions, treatment with TFA, would degrade the phosphoryl derivatives.

Global phosphorylation involves the post-synthetic phosphorylation of unprotected hydroxyl residues on the solid support (Andrews, D. W. (1991). International Journal of Peptide and Protein Research 38, 469.; Kitas et al., 1991; Otvos, L., Elekes, I., and Lee, V. M. Y. (1989) Solid-Phase Synthesis of Phosphopeptides. International Journal of Peptide and Protein Research 34, 129-133.; Perich, J. W., and Johns, R. B. (1988) Australian Journal of Chemistry 43, 1623) or in solution (Perich, J. W., and Johns, R. B. (1988) Di-Tert-Butyl N,N-Diethylphosphoramidite and Dibenzyl N,N-Diethylphosphoramidite-Highly Reactive Reagents For the Phosphite-Triester Phosphorylation of Serine-Containing Peptides, Tetrahedron Letters 29, 2369-2372). The post-synthetic phosphorylation strategy provides both the phosphorylated and unphosphorylated peptide in the same synthesis. In this approach, residues to be phosphorylated are most commonly incorporated without protection of the hydroxyl groups. This generally requires the use of less active acylating agents to avoid hydroxy acylation (Andrews, 1991; Debont, H. B. A., Vanboom, J. H., and Liskamp, R. M. J. (1990) Automatic Synthesis of Phosphopeptides by Phosphorylation on the Soild-Phase, Tetrahedron Letters 31, 2497-2500; Kitas et al., 1991; Otvos et al., 1989; Perich et al., 1991). Side reactions have been reported (Yon, M. (1994) In Innovations and Perspectives in Solid Phase Synthesis, 1993: Biological and Biomedical Applications, R. Epton, ed. (Birmingham: Mayflower Worldwide Ltd.), pp. 707), and the potential for undesired reactions increases with each coupling cycle. Thus, it is desirable to protect the reactive hydroxyl functionalities until phosphorylation. Complications in the coupling phase of the synthesis can be avoided by protecting the hydroxyl side chains as the trityl ethers. The trityl group can be removed without affecting the typical resin linkage used in Fmoc-based solid state peptide synthesis or other acid labile protecting groups; thus enabling a selective solid supported global phosphorylation step.

The global phosphorylation strategy typically employs phosphorylation reagents developed for oligonucleotide synthesis. For example, phosphorylation can be accomplished by reaction with a phosphochloridate (Hormozdiari, P., and Gani, D. (1996). Highly efficient solid-phase phosphopeptide synthesis using bis-(polyfluorophenyl) chlorophosphates: Preparation of serine-threonine protein phosphatase substrates. Tetrahedron Letters 37, 8227-8230; Otvos et al., 1989) or H-phosphonate (Larsson, E., and Luning, B. (1994). Solid-Phase Phosphorylation of a Peptide By the H-Phosphonate Method. Tetrahedron Letters 35, 2737-2738) followed by oxidation (in the case of the H-phosphonate) and cleavage of the phosphate ester protecting groups. Another method involves reaction of the partially protected peptide with a phosphoramidite (Perich and Johns, 1988), followed by oxidation of the intermediate phosphite, and deprotection of the phosphate moiety.

The synthesis of sulfate-containing peptides is generally more difficult than that of the analogous phosphorylated peptides. The difficulties are at least in part due to the greater acid lability of the aryl sulfate ester (Fields, G. B., Tian, Z., and Barany, G. (1992) In Synthetic Peptides. A User's Guide, G. A. Grant, ed. (New York: W. H. Freeman and Co.), pp. 77-183).

Several strategies have been developed for the synthesis of Tyr-sulfated peptides, Post-assembly sulfation has been reported in which a peptide is first synthesized containing a single nonsulfated or protected Tyr residue and thereafter the single Tyr residue is sulfated following selective deprotection if necessary. The N-terminal amino group and the hydroxyl groups of any Ser and Thr residues and in some cases the side-chain amino groups are protected during sulfation. Okada, Y. (2001). Synthesis of peptides by solution methods. Current Organic Chemistry 5, 1-43. reported a low yield synthesis of porcine cholecystokinin-33 (CCK-33) which contains a single sulfated Tyr at position 27. The peptide also contains five serine residues as well as tryptophan and arginine residues. The peptide was assembled with the side chains of these amino acid residues protected with base labile protecting groups. The free Tyr residue was sulfated and the protecting groups removed.

Yajima and coworkers (Fujii, N., Futaki, S., Funakoshi, S., Akaji, K., Morimoto, H., Doi, R., Inoue, K., Kogire, M., Sumi, S., Yun, M., To be, T., Aono, M., Matsuda, M., Narusawa, H., Moriga, M., and Yajima, H. (1988). Studies On Peptides 160 Synthesis of a 33-Residue Peptide Corresponding to the Entire Amino-Acid Sequence of Human Cholecystokinin (HCCK-33). Chemical & Pharmaceutical Bulletin 36, 3281-3291) reported another low yield synthesis of human CCK-33 involving global deprotection of the assembled protected peptide, followed by Fmoc reprotection of free amino groups, selective protection of hydroxyl groups of Ser and Trp residues with t-butyldiphenylsilyl groups (TBDPS) and sulfation of the single Tyr phenolic OH with pyridine.$SO_3$ complex with simultaneous deprotection of the Fmoc and TBDPS groups with tetra-n-butylammonium fluoride.

Kitagawa and coworkers reported the synthesis of CCK-12 using an orthogonal protection scheme for sulfation of a single tyrosine residue in partially protected peptide Futaki, S., Taike, T., Akita, T., and Kitagawa, K. (1992) Synthese of 2 Tyrosine Sulfate Containing Peptides, Leucosulfakinin (LSK)-II and Cholecystokinin (CCK)-12, Using the O-Para-ethylsulphinyl)Benzyl Serine for the Selective Sulfation of Tyrosine. Tetrahedron 48, 8899-8914) employing a safety catch-type protecting group to block alcoholic groups during peptide synthesis. The p-methylsulfinyl benzyl ether (Msib) ether group was used to block a serine side chain, and the corresponding carbamate (Msz) was used as the N-terminal α-amino protecting group. The p-methylsulfinyl benzyl group withstands treatment with TFA, but upon reduction to the thioether becomes acid labile. Standard Fmoc-based peptide synthesis using t-Bu protected tyrosine was employed to assemble the protected dodecapeptide, which was then cleaved from the resin using TFA which also removed all other protecting groups except the p-methylsulfinyl benzyl groups. Free tyrosine was then sulfated with DMF.SO$_3$ complex and the sulfinyl groups were reduced with ethane dithiol. The Asp and Trp side chains were not reprotected before sulfation. The protected, sulfated peptide was purified by gel-filtration and final deprotection was accomplished using 90% aqueous TFA. A 6% yield of sulfated peptide after HPLC purification was reported.

Matsubayashi et. al. reported the synthesize of active fragments of the sulfated plant growth factor peptide, phytosulfokine (Matsubayashi, Y., Hanai, H., Hara, O., and Sakagami, Y. (1996). Active fragments and analogs of the plant growth factor, phytosulfokine: Structure-activity relationships. Biochemical and Biophysical Research Communications 225, 209-214). Standard Fmoc-based peptide chemistry was employed, and FmocTyr was used directly in chain elongation without special precautions or protection of the phenolic hydroxyl. The support-bound intermediates were then sulfated and the sulfated peptides were cleaved from the solid support with concomitant global deprotection of acid labile Boc, t-butyl and trityl protecting groups. A yield was not reported. This strategy is unlikely to be general due to potential side reactions of the free phenolic hydroxyl during peptide synthesis (Jones, J. (1994). The chemical synthesis of peptides (Oxford: Oxford University Press); Stewart, J. M. (1981). In The Peptides, E. Gross and J. Meienhofer, eds. (London: Academic Press), pp. Chapter 4) and degradation of the sulfotyrosine residues during the acidic cleavage/deprotection reaction.

Sulfotyrosine residues can be incorporated directly into the peptide backbone during the peptide synthesis stage. The Boc strategy for peptide synthesis is not compatible with this approach since iterative treatment with strong acid would desulfate any sulfotyrosine residues present during elongation and the resin cleavage protocol would destroy any sulfate groups. The milder conditions employed with the Fmoc strategy for peptide synthesis allow sulfotyrosine incorporation via direct coupling of FmocTyr(SO$_3$) during peptide synthesis. Penke and Rivier employed this strategy as a part of a general investigation of new, solid phase routes to acid-sensitive peptides (Penke, B., and Rivier, J. (1987). Solid-Phase Synthesis of Peptide Amides On a Polystyrene Support Using Fluorenylmethoxycarbonyl Protecting Groups. Journal of Organic Chemistry 52, 1197-1200). Using a 2,4-dimethoxybenzhydrylamine linker for the polystyrene resin, they report the synthesis of cholecystokinin octapeptide (CCK-S, Asp-Tys-Met-Gly-Trp-Met-Asp-Phe-NH$_2$, where Tys is sulfated Tyr). The cleavage required a 15 minute treatment with TFA-thioanisole (8:2). Interestingly, the use of 7% 4-(methylthio)phenol in TFA resulted in complete desulfation. The product mixture was described by the authors as, "containing mostly CCK-8 and nonsulfated CCK-S." However, neither yields for the two peptides nor the ratio of sulfated to nonsulfated peptide were reported.

Kitagawa and coworkers (Kitagawa, K., Futaki, S., and Yagami, T. (1994). A Novel-Approach for the Synthesis of Tyrosine Sulfate-Containing Peptides Using a Safety Catch Type Protecting Group as a Key Feature. Journal of Synthetic Organic Chemistry Japan 52, 675-685) reported the synthesis of an octapeptide, cionin, using the standard Fmoc-based chemistry (Atherton, E., and Sheppard, R. C. (1989). Solid Phase Peptide Synthesis, A Practical Approach (Oxford: IRL Press at Oxford University Press)) and the acid sensitive PAL-resin (Albericio, F., Kneibcordonier, N., Biancalana, S., Gera, L., Masada, R. I., Hudson, D., and Barany, G. (1990). Preparation and Application of the 5-(4-(9-Fluorenylmethyloxycarbonyl)Aminomethyl-3,5-Dimethoxyphenoxy) Valeric Acid (Pal) Handle For the Solid-Phase Synthesis of C-Terminal Peptide Amides Under Mild Conditions. Journal of Organic Chemistry 55, 3730-3743) as the support for direct, stepwise incorporation of Tyr(SO$_3$Na) residues into the peptide chain. The deprotection conditions were reported to be mild enough to minimize the deterioration of the sulfate moiety. However, detachment of the peptide amide from the polymer support was incomplete (about 40%) under these conditions, and the protocol was said by the authors to be "not suited to synthesis of longer peptides."

The sulfated peptide CCK-8 (Asp-Tys-Met-Gly-Trp-Met-Asp-Phe-NH, SEQ ID NO:1) was reported to be synthesized using standard Fmoc chemistry (Han, Y. X., Bontems, S. L., Hegyes, P., Munson, M. C., Minor, C. A., Kates, S. A., Albericio, F., and Barany, G. (1996). Preparation and applications of xanthenylamide (XAL) handles for solid-phase synthesis of C-terminal peptide amides under particularly mild conditions. Journal of Organic Chemistry 61, 6326-6339) with incorporation of the tyrosine sulfate residue accomplished directly by coupling the barium salt of Fmoc Tyr(SO$_3$). The two aspartate residues were protected as allyl esters and deprotected upon completion of chain assembly by palladium-catalyzed allyl transfer. The peptide was cleaved from the support with TFA-CH$_2$Cl$_2$—H$_2$O (1:18:1). The overall cleavage yield was reported to be 71% and desulfation was reported to be negligible.

This invention relates, in certain embodiments, to glycopeptide synthesis. Various methods for glyopeptide synthesis are known in the art. Leppanen et al. (Leppanen, A., White, S. P., Helin, J., McEver, R. P., and Cummings, R. D. (2000). Binding of glycosulfopeptides to P-selectin requires stereospecific contributions of individual tyrosine sulfate and sugar residues. Journal of Biological Chemistry 275, 39569-39578) described the synthesis of glycosulfopeptides. Their studies indicated inefficient synthesis using stepwise incorporation of FmocTyr(SO$_3$Na). Thus, they initially resorted to the enzyme, TPST, to introduce the sulfate groups. This enzyme showed no selectivity between tyrosines in the sulfation reaction and did not allow the preparation of the mono and di-sulfated peptides. The desired sulfated peptides were reported to be successfully synthesized using Wang resin and stepwise incorporation of FmocTyr(SO$_3$Na). This approach differs from the enzyme-mediated sulfation because the site of sulfotyrosine incorporation can be chosen. However, details of the synthesis were not reported and the method was described as "inefficient."

Kitagawa and coworkers employed the 2-chlorotrityl linker for the synthesis of sulfated peptides via the stepwise approach, using Fmoc Tyr[SO$_3$H] as a building block (Kitagawa, K., Aida, C., Fujiwara, H., Yagami, T., and Futaki, S. (1997). Efficient solid-phase synthesis of sulfated tyrosine-containing peptides using 2-chlorotrityl resin: Facile synthesis of gastrin/cholecystokinin peptides. Tetrahedron Letters 38, 599-602). Other polar amino acid side chains were protected using the standard acid labile groups used for Fmoc-based peptide synthesis. A two part cleavage/deprotection protocol was reported with cleavage from the support accomplished with AcOH-trifluoroethanol-CH$_2$Cl$_2$ (1:1:3)v/v, followed by deprotection with 90% aqueous TFA at 4° C. for five hours. Desulfation was reportedly negligible during the cleavage from the resin. Remarkably, the latter acid treatment at low temperature was reported to result in minimal deterioration of the sulfate group (ca. 10% as judged by HPLC).

Methods for synthesis of glycopeptides and proteins have been reported. Recent reviews of these methods, starting materials and reagents for synthesis are provided in Davis B.

G. (2002) Synthesis of Glycopeptides *Chem. Review* 102: 579-601; Hojo H and Nakahara Y. "Recent progress in the solid-phase synthesis of glycopeptide," Curr Protein Pept Sci. July 2000; 1(1):23-48; Schultz M, and Kunz H, "Chemical and enzymatic synthesis of glycopeptides," EXS. (1995) 73:201-228; and Meldal M, and St Hilaire PM. "Synthetic methods of glycopeptide assembly, and biological analysis of glycopeptide products," 1997 Curr. Opinion Chem. Biol. December 1(4):552-563. Methods described include the use of solid phase methods employing glycosylated amino acid residues to synthesize O- and N-linked glycopeptides and glycosylation of resin bound peptide. Luning B, Norberg T, and Tejbrant J. "Synthesis of mono- and disaccharide aminoacid derivatives for use in solid phase peptide synthesis," (1989) Glycoconj. J. 6(1):5-19 reports certain protected glycosylated amino acids useful in solid phase peptide synthesis.

While methods for synthesis of modified peptides and proteins, particularly for sulfation, phosphorylation and glycosylation are available in the art, there remains a need in the art for more efficient, higher yield and less complex synthetic methods and there remains a need for improved methods for the selective modification of a subset of similar or analogous sites in a peptide or protein.

SUMMARY OF THE INVENTION

This invention provides methods and protected amino acids useful as building blocks (e.g., protected monomers) for the synthesis of peptides and proteins that are selectively modified at one or more side-chain hydroxyl groups. The invention is based, at least in part, on the use of azide-bearing protecting groups that allow the selective deprotection of side-chain hydroxyl groups of amino acids after synthesis of a peptide or protein. Reaction conditions for removal of the azide-bearing protecting group can be selected which are substantially orthogonal to those that will remove α-amino protecting groups typically employed in peptide synthesis, e.g., Fmoc and Boc, such that hydroxyl groups protected with the azide-bearing protecting group remain protected during synthesis of the peptide chain. Various protecting groups which are readily available can be used for protecting potentially reactive side chain groups of amino acids in the peptide or protein to be modified. Preferred side-chain protecting groups are chemically distinguishable from the azide-bearing protecting group and substantially orthogonal reaction conditions can be selected such that side-chain protection of other amino acids is maintained when the azide-bearing protecting group is removed. The use of the azide-bearing protecting group of this invention for one or more hydroxy amino acids during peptide synthesis-allows the selective unmasking of those azide-protected side-chain hydroxyl groups and selective modification of the hydroxyl groups that are selectively unmasked.

The methods and protected amino acids of this invention can be employed for selective modification to attach various groups to selected side-chain hydroxyl groups; for example, the method can be used for selective sulfation, phosphorylation and/or glycosylation at selectively unmasked hydroxyl group(s). The method and protected amino acids of this invention can specifically be used to selectively modify fewer than all of the side-chain hydroxyl groups of a peptide or protein and can be used to select the pattern (spacing, number and type of modifications) of modification along the peptide chain.

More specifically, the invention provides methods for the synthesis of peptides and proteins that are modified at the hydroxyl group of one or more tyrosine, serine and/or threonine residues. The invention is specifically implemented employing protected tyrosine, serine and/or threonine starting materials in which one or more of the side-chains is protected with an azide-bearing protecting group. In those cases in which fewer than all of the hydroxyl amino acids in a peptide or protein are to be modified, hydroxy amino acids protected using a chemically distinguishable protecting group that is not removed under the reaction conditions selected for removal of the azide-bearing protecting group are employed in combination with the azido protected hydroxy amino acids.

In the method of this invention a modified peptide or protein is synthesized by:

providing a peptide or protein comprising one or more hydroxy amino acid residues wherein the hydroxyl group of at least one of the hydroxy amino acid residues in the peptide is protected with an azide-bearing protecting group, wherein the α-amino group of protected amino acids used to synthesize the peptide or protein are protected with a protecting group which can be removed under selected reaction conditions which do not substantially remove the azide-bearing protecting group and wherein potentially reactive side-chain groups in the amino acids of the peptide or protein, other than the hydroxy groups protected with the azide-bearing protecting group, are protected with one or more protecting groups which are not substantially removed under reaction-conditions selected for removal of the azide-bearing protecting group;

deprotecting the hydroxy amino acid residues of the one or more azido protected residues in the peptide under conditions such that one or more free hydroxyl groups are generated and such that other protecting groups in the peptide or protein are not substantially removed; and functionalizing the one or more free hydroxyl groups to generate the modified peptide.

In general, the free (i.e., unmasked or deprotected) hydroxyl groups generated by removal of the azide-bearing protecting group can be functionalized by use of any reaction that converts a hydroxyl group to a useful functional group, e.g., to convert the OH group to an optionally substituted alkoxy or aryloxy group, to convert the OH to a sulfate group to generate a sulfated peptide residue, to convert the OH to a phosphate group to generate a phosphorylated peptide residue, or to add a saccharide to generate a glycosylated peptide. The free hydroxyl group can also be functionalized with any group that provides a detectable label, e.g., a fluorescent label, a radiolabel, an isotopic label (a group that is enriched in one or more selected normally low-abundance isotopes, e.g., deuterium, tritium, $^{13}C$, $^{15}N$, $^{18}O$, $^{37}Cl$, $^{32}P$, $^{35}S$, etc.). In a specific embodiment, the protected amino acid contains an optionally substituted phenol which is unmasked on removal of the azide-bearing protecting group. In a more specific embodiment, the protected amino acid is a tyrosine and the phenol group of the tyrosine is unmasked by removal of the azide-bearing protecting group.

The peptide or protein carrying selective protection of one or more side chain hydroxyl groups with an azide-bearing protecting group can be provided by any known method of peptide and or protein synthesis that allows selective incorporation of the azide-bearing protecting group. Solution-phase and preferably solid-phase methods for peptide synthesis can be employed to generate selectively protected peptides. Selectively labeled proteins can be provided by means known in the art, and specifically by art-known methods from selectively protected peptides prepared by solution-phase and more preferably solid-phase peptide synthesis. Preferred methods of peptide synthesis useful in the methods of this invention are Fmoc-based methods and Boc-based methods.

The selectively protected peptide or proteins carrying one or more azide-bearing protecting groups can carry additional protecting groups, including amino protecting groups and side-chain protecting groups as noted above.

In a preferred embodiment the selectively protected peptide of this invention is provided by solid phase peptide synthesis (SPPS) employing one or more hydroxy amino acid building blocks in which the hydroxyl group of the amino acid side chain is protected with an azide-bearing protecting group. The α-amino protecting group must be removable under selected reaction conditions that are substantially orthogonal to reaction conditions that can remove the azide-bearing protecting group. Additionally, in cases where SPPS is employed, reaction conditions selected for removal of the azide-bearing protecting group are preferably substantially orthogonal to reaction conditions that cleave the growing peptide from the solid support or resin employed such that the peptide remains attached to the solid support or resin during modification steps. Hydroxy amino acids in the protected peptide which are not intended to be modified are protected with a hydroxyl protecting group that is chemically distinct from the azide-bearing protecting group and that is not substantially removed under selected reaction conditions that remove the azide-bearing protecting group employed. Similarly potentially reactive groups in other amino acids in the peptide are protected with protecting groups that are chemically distinct from the azide-bearing protecting group and that are not substantially removed under selected reaction conditions that remove the azide-bearing protecting group employed. The azide-bearing protecting group of this invention is preferably removed under mild reducing conditions employing $SnCl_2$. Protected proteins of this invention are preferably prepared by methods known in the art by solid phase synthesis or by coupling of peptides synthesized using solid phase methods.

The synthesis of peptides and proteins of this invention may be in whole or in part machine-aided, for example conducted using an automated peptide synthesizer. Standard automated peptide synthesis can be readily adapted for conducting the method of synthesis of modified peptides of this invention.

Generally the method of this invention employs one or more protected hydroxy amino acids of the formula:

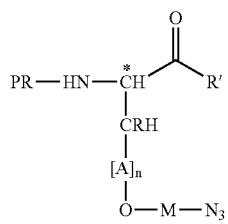

and salts thereof wherein:
  * indicates that the C may be chiral non-racemic or racemic;
  —O-M-$N_3$ is the azide-bearing protecting group where:

M is selected from:
  —$(CR_2)$—$_m$ where m is 1-6 and preferably m is 1-3;
  —$CH_2$-phenyl-, where the phenyl group can be optionally substituted;
  —$CH_2$-phenyl-O—, where the phenyl group can be optionally substituted;
  —CO—NH—$CH_2$—$CH_2$—; or
  —CO—NH—$SO_2$—$CH_2$—$CH_2$—;

PR is any appropriate amine protecting group wherein the conditions for removal of PR are substantially orthogonal to conditions selected for removal of the azide-bearing protecting group —O-M-$N_3$;

A is an optionally substituted phenyl group; and n is 1 or 0 to indicate the presence or absence of the A moiety;

R' is OR, OAr, OR", halide (e.g., F, Cl or Br); $NR_2$, N(R)(Ar), N(Ar)$_2$

R is H or an optionally substituted alkyl, alkenyl, alkynyl or aryl group,

Ar is an optionally substituted aryl group; and

R" is a group that makes —COOR" an activated ester group, e.g., where R" can, among others, be a substituted phenyl, e.g., a pentahalophenyl (e.g., pentafluorophenyl or pentachlorophenyl), a trihalophenyl (e.g., 2,4,5-trichlorophenyl), a nitrophenyl group (e.g., p-nitrophenyl), a benzotriazol-1-yl, succinimido, or a 3,4-dihydro-4-oxo-1,2,3-benzotriazin-3-yl group.

Compounds of the above formula may be D- or L-isomers or racemic.

In specific embodiments, R is $CH_3$ and n is 0 (protected threonines), R is H and n is 0 (protected serines) or R is H and n is 1 (protected tyrosines).

Protecting groups other than the azide-bearing protecting group, conditions for various synthetic reaction steps for peptide synthesis, coupling reagents (e.g., carbodiimides, uronium salts or phosphonium salts), solid support (e.g., resin), linker groups, methods for modification (e.g., sulfation, phosphorylation and/or glycosylation methods) as well as methods for isolation and purification of modified peptides and proteins can be selected generally as known in the art in view of the descriptions herein with respect to the azide-bearing protecting groups and its uses.

In specific embodiments, M is a —$CH_2$— group (the protecting group is azidomethylene).

In another specific embodiment M is a —$CH_2$—$CH_2$— group.

In specific embodiments, M is not a —$CH_2$-Phenyl-O— group with optional substitution on the phenyl ring.

In specific embodiments, PR can be an acid-labile protecting group, a base-labile protecting group, or a sulfonyl protecting group. More specifically PR can be certain alkoxyl carbonyl groups including e.g., a Boc, Bpoc, or Fmoc group or Fmoc derivatives, protecting groups containing xanthenyl groups (U.S. Pat. No. 5,101,059), a 2-nitrosulfonyl group, a dithiasuccinoyl group, a diphenylphosphinyl group, or a sulfonyl group, or derivatives thereof. Other appropriate protecting groups can be readily selected by those of ordinary skill in the art based on what is well-known in the art and the teachings herein.

In preferred embodiments, PR is an Fmoc group or a derivative thereof or PR is a Boc group.

The invention also provides kits for the synthesis of peptides and proteins modified at side-chain hydroxyl groups which comprise one or more of the protected hydroxy amino acids of the above formula. Preferred protected hydroxy amino acids are those in which M is —$CH_2$—. Preferred protected hydroxy amino acids are those in which PR is Fmoc or Boc. The kit can further contain amino acids for peptide synthesis with α-amine group protection, optional side-chain protection (other than the azide-bearing protecting group) and optional carboxy group protection and/or activation as appropriate for use with PR and the azide-bearing protecting group of the protected hydroxy amino acid or acids provided in the kit. The kit may further contain reagents for deprotection of the azide-bearing protecting group or for deprotection of other protecting groups. The kit may also include solid support materials, e.g., a resin, appropriate for conducting peptide synthesis employing the protected amino acid or acids provided in the kit. The kit may further provide reagents for modification of the selected hydroxy amino acid, e.g., reagents for sulfation, phosphorylation and/or glycosylation. The kit may further provide instructions for conducting peptide synthesis and for selective modification of the peptide. Kits may further comprise solvents and other reagents for conducting peptide synthesis. Kits can contain selected amounts of individual components to provide relative amounts of components for conducting a selected reaction or synthesis. The kit may contain specific instruction for combination of kit components to conduct a selected reaction or synthesis. Kit components may be provided in separate individual containers. A given kit may contain one or more containers carrying a pre-selected amount of any given component. The invention further provides a method of synthesizing a modified peptide or protein employing a kit of this invention.

BRIEF DESCRIPTION OF THE DRAWINGS

FIG. 1 is the chemical structure of an exemplary protected tyrosine monomer for use in the methods herein having an azide-bearing protecting group, FIG. 2 is a scheme for the synthesis of a protected tyrosine monomer having an azide-bearing protecting group exemplified for the synthesis of the compound of FIG. 1A. In the scheme illustrated, conditions for step a are KOt-Bu, NaI, $CH_3SCH_2Cl$, DMF, specific yield for 3 is 82%; for step b, e.g. to make 4, are: NCS, TMSCl, $CH_2Cl_2$; for step c to make 5 are $NaN_3$, DMF, $H_2O$, with specific yield over steps b and c to make 5 of 87%; for step d: TMSOTf, $CH_2Cl_2$; for step e: FmocOSu, $Et_3N$, THF (in synthesis of 1, the yield over steps d and e was 84%) and for step f: LiOH—$H_2O$, THF-$H_2O$, 0° C. (with a specific yield for 1 of 88%).

FIG. 3 is an exemplary scheme for sulfated peptide synthesis.

DETAILED DESCRIPTION OF THE INVENTION

Figure 4A:
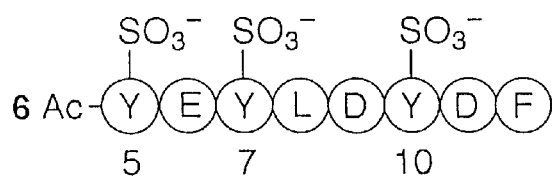
FIGS. 4A and 4B are structures for sulfated peptide targets 6 (SEQ ID NO:2) and 7 (SEQ ID NO:3).

The methods of this invention employ an azide-bearing protecting group, particularly an azidomethylene protecting group, which is stable under acidic and basic conditions that can be used to remove protecting groups typically employed in peptide synthesis, such as Fmoc, t-Boc, and benzyl protecting groups. The azide-bearing protecting group is thus removable under conditions that are substantially orthogonal to those used to remove other protecting groups used in peptide synthesis and provides additional synthetic flexibility for peptide and protein synthesis. In particular, the azide-bearing protecting group can be employed as orthogonal protection for hydroxyl groups of amino acid side chains. The use of the azide-bearing protecting group allows selective modification of peptides or proteins at one or more hydroxyl groups of the amino acid residues.

Solid phase peptide synthesis generally proceeds by initial attachment of a first α-amino protected amino acid to a solid support (typically a resin) at its carboxylic acid end via a linker. Resins with certain protected amino acids already attached are available from commercial sources or can be synthesized by art known methods. The α-amino protecting group is removed from the resin linked amino acid and a second α-amino protected amino acid is coupled to the first amino acid using a coupling agent. Cycles of deprotection and coupling of protected amino acids continue until the desired peptide sequence is prepared. The reaction conditions (reagent, concentration, solvent, temperature, time, etc.) of deprotection of the α-amino protecting group selected for synthesis preferably do not cleave a substantial amount of the growing peptide from the resin selected for synthesis. Potentially reactive groups on the side chains of protected amino acid synthetic peptide building blocks may also be protected, typically with protecting groups that are not substantially removed by the reactions conditions selected for removal of the α-amino protecting group and those selected for removal of the azide-bearing protecting group. A variety of protecting groups, reaction conditions for deprotection, coupling agents, reaction conditions for coupling linkers, resins, and conditions for cleavage of the peptide from the resin are known in the art. Specific examples of protecting groups, reaction conditions for deprotection, coupling reagents, coupling reaction conditions, resins and cleavage conditions are found in references cited herein and incorporated by reference herein.

Details of solid phase peptide synthesis are given, for example, in Greene, T. and Wut, P. *Protecting Groups in Organic Synthesis*, Wiley Science, 1984 and later editions; Atherton, E. and Sheppard, R. C. (1989) in *Solid-Phase Peptide Synthesis. A Practical Approach*, IRL Press at Oxford University Press; Barany et al. (1987) Int. J. Peptide Protein Res. 30:705-739. The details of SPPS using the base labile protecting group Fmoc (N-fluoren-9-yl-methoxycarbonyl) are provided in Chan, W. C. and White P. D. (2000) in *Fmoc-Solid Phase Peptide Synthesis, A Practical Approach*, IRL Press at Oxford University Press. More details on various linkers and solid supports for use in SPPS are provided in Domer et al. (1999), "Solid-phase organic chemistry: linkers and functionalized solid supports," *Chimia* 53:11-17. More details of coupling reagents are provided in Albericio, F. and Carpino, L. A. (1997), "Coupling reagents and activation," in *Solid Phase Peptide Synthesis, Methods in Enzymology* 201:104-126; Erlich, A. et al. (1996) J. Org. Chem. 61(25):8831-8838; and Carpino et al. (1996) J. Org. Chem. 161(7):2460-2465.

The doctoral thesis of T. Young, (2000) University of Wisconsin (Madison) which is incorporated by reference herein, also contains a discussion of solid phase peptide synthesis (SPPS) particularly Boc-based and Fmoc-based methods and further contains a discussion of the 2-clorotrityl linker used in solid phase peptide synthesis. The thesis provides examples of protecting groups useful for side group protection in SPPS.

Fmoc and related derivatives thereof are described in U.S. Pat. Nos. 3,839,936; 3,835,175; and 4,108,846. Protecting groups that are removable under conditions orthogonal to those that remove Fmoc are described in U.S. Pat. No. 5,101,059. Sulfonyl protecting groups are exemplified in U.S. Pat. No. 5,942,601.

The term "orthogonal" as applied to reaction conditions for removal of a protecting group or cleavage of a peptide from a support refers to the following situations:

the reaction conditions selected and useful for cleaving a bond to a first protecting group to remove that first protecting group do not cleave another bond to a second protecting group to remove the second protecting group, i.e., the reaction conditions selected for removal of the first protecting group are orthogonal to the conditions needed for removal of the second protecting group;

the reaction conditions selected and useful for cleaving a bond to a protecting group to remove that protecting group do not cleave a bond linking the peptide synthesized to the solid support (e.g., resin) selected for SPPS, i.e., the reaction conditions selected for removal of the protecting group are orthogonal to the conditions needed for cleaving a peptide from a support; or the reaction conditions selected and useful for cleaving a bond linking a peptide synthesized to a solid support (e.g., resin) selected for peptide synthesis do not cleave a bond to a protecting group to remove that protecting group i.e., the reaction conditions selected for cleavage of the peptide from the solid support are orthogonal to the conditions needed for removal of the protecting group.

While it is preferred that the removal of a given protecting group or a given bond cleavage not occur when orthogonal conditions are employed, relatively low amounts of undesired deprotection or cleavage may occur without significant detriment to synthesis by the method herein. This situation is referred to herein as "substantially orthogonal" conditions.

It may be the case that the reaction conditions for removal of a first and a second protecting group are mutually orthogonal, i.e., the reaction conditions selected for removal of the first protecting group do not remove the second protecting group and the reaction conditions selected for removal of the second group do not remove the first group (e.g., where one group is acid labile and the other base labile). For example, each side-chain protecting group employed and any α-amino protecting group employed in peptide synthesis may be removable using mutually orthogonal reaction conditions. Similarly, it may be that conditions selected for removal of a selected protecting group do not cleave the peptide from a selected resin and that selected reaction conditions for cleavage of the peptide from a selected resin do not remove the selected protecting group. The term "mutually orthogonal" is used herein to refer to this two-way orthogonality of reaction conditions for removing different protecting groups and cleavage of the peptide from a support.

As used herein, the term "quasi-orthogonal" (including substantially quasi-orthogonal) includes situations in which a first bond (attaching a protecting group or linking a peptide to a solid support) can be cleaved under conditions that do not cleave a second bond (attaching another protecting group or linking a peptide to a solid support), but that any conditions sufficient for cleavage of the second bond would also cleave the first bond. For example, a first protecting group may be selectively removed, in relation to a second protecting group, under weakly acidic conditions, while the second protecting group may only be removed under more strongly acid conditions that also remove the first protecting group. The term orthogonal is intended to encompass both one-way and two-way orthogonality. "Mutually orthogonal" refers to two-way orthogonality of reaction conditions of two steps and "quasi-orthogonal" refers to one-way orthogonality of reaction conditions of two steps.

Reaction conditions refer to all reaction parameters that may be varied to change reactivity, including time, temperature, solvent, choice of reagent or reagents, concentrations of reactants and/or reagents, addition or removal of catalyst, change of catalyst, pH, ionic strength, pressure, etc. In principle, reaction conditions can be orthogonal because of a variation in any reaction parameter, but more typically are orthogonal because they employ different types of reagents (e.g., an acid vs. a base), different strengths of reagents (e.g., a weakly reducing agent vs. a strongly reducing agent) different pH or different concentrations of reagents (e.g., low concentration of acid vs. high concentration of acid.)

The terms peptides and proteins refer to oligomers and polymers, respectively, of amino acids bonded through peptide bonds and are intended to encompass peptides and proteins formed from any amino acids including α-amino acids, β-amino acids, γ-amino acids, δ-amino acids, naturally occurring amino acids, and non-naturally occurring amino acids. The terms peptides and proteins generally include those that are derivatized having modifications of side-chains such as sulfation, phosphorylation and glycosylation as well as those having modified or functionalized amino termini and/or carboxy termini.

The methods of this invention can also be readily adapted and applied to the synthesis of peptidomimetics, such as those formed from N-alkyl amino acids (e.g., peptoids). In exemplary applications, N-alkyl amino acids having hydroxy side-chains analogous to those in the formula above are used in peptidomimetic synthesis:

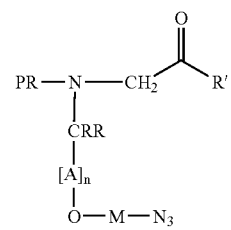

and salts thereof where variables PR, R, R', M, A, and n are as defined above.

Alpha-amino protecting groups, any carboxylic acid protecting or activating groups, any side-chain protecting groups, any solid supports, any linkers, coupling reagents and reaction conditions for synthesis steps are generally selected as is known in the art for synthesis of peptides with the proviso that the selected materials and methods are compatible with the use of the azide-bearing protecting groups described herein. Note that more than one α-amino protecting group, and more than one side-chain protecting group (for a given amino acid residue) may be employed in the synthesis of a given modified peptide or protein. Similarly, more than one coupling reagent may be used during synthesis and reaction conditions for a given step may be modified during the synthesis if desired.

Amino acids useful in the synthetic methods of the invention may contain side chain protection as is known in the art. Side-chain protection is selected as is known in the art with the proviso that the side-chain protecting groups selected are compatible for use in the synthesis with the azide-bearing protecting group of this invention.

Various coupling reagents as generally known in the art of peptide synthesis may be employed in the methods of this invention with the proviso that the coupling reagent is compatible with the use of the azide-bearing protecting group of this invention and the desired modification reaction. Useful coupling reagents include, among others, carbodiimides (e.g., DCC, DIC, EDCI, DCC/HOBt), uronium salts (e.g., HBTU, HATU) and phosphonium salts (e.g., BOP, pyBOP, pyAOP). Throughout the specification standard abbreviations are employed for various protecting groups and coupling agents.

In general, the selective modification of unmasked hydroxy groups of hydroxy amino acid residues can employ any known methods that are compatible with the protecting groups, any solid support, and any linker in the peptide or protein provided or as used in synthesis of the peptide or protein to be modified.

The terms "alkyl", "alkenyl" and "alkynyl" are used as they are in the art and are intended broadly to include straight-chain, branched or cyclic groups. Alkyl groups are saturated hydrocarbon groups. Alkenyl groups are hydrocarbon groups having one or more double bonds. Alkynyl groups are hydrocarbon groups having one or more triple bonds. Preferred alkyl, alkenyl and alkynyl groups have one to six carbon atoms, more preferred alkyl groups have one to three carbons. Alkyl, alkenyl, and alkynyl groups may be optionally substituted as described below.

The term "aryl" is used in variable definitions herein broadly to include groups having at least one aromatic ring which may be heterocyclic (contain one or more non-carbon atoms). Aryl groups may contain alkyl portions. Aryl groups may contain two or more rings at least one of which is aromatic. A phenyl group is an exemplary aryl group. Aryl groups may be optionally substituted as described below.

Alkyl groups, aryl groups and phenyl groups of the compounds of this invention may be optionally substituted with any functional groups that do not interfere with (or which can be protected from interfering with) the steps of peptide or protein synthesis as described herein. Specific substituents include, among others, halides (e.g., F, Cl, Br), nitro groups, CO on rings or inserted into carbon chains, —COR, —COOR, or alkoxy groups (alkyl-O—). Optional substitution can also include OH groups, or amino (—NR$_2$) groups which may require the use of additional protecting groups.

Protected amino acid building blocks of this invention can be synthesized employing the methods described herein and in Young, T. Doctoral Thesis 2001, supra or by routine modification of those methods in view of what is known in the art.

The methods of this invention provide for selective modification of hydroxyl groups in side chains of amino acids and specifically relate to modifications of tyrosine, serine, and/or threonine residues. Any desired modification of such hydroxyl groups is encompassed by this invention. Those of ordinary skill in the art can employ known methods for modification at such hydroxyl groups in the practice of this invention as broadly described herein. Of particular interest are sulfation, phosphorylation and glycosylation at hydroxyl groups of amino acid side chains.

Methods for sulfation useful in combination with the selective deprotection methods provided herein are known in the art. Specific sulfation reagents that can be applied include, among others, any SO$_3$ equivalent including SO$_3$ (e.g., DMF.SO$_3$, pyridine.SO$_3$, Me$_3$N.SO$_3$), a tertiary ammonium salt of acetyl sulfuric acid (see: U.S. Pat. No. 4,444,682), and DCC/H$_2$SO$_4$.

Methods for phosphorylation useful in combination with the selective deprotection methods provided herein are known in the art. Additional detail for such methods can be found in Synthesis Notes NovaBiochem Catalog 2002/2003 (Calbiochem-NovaBiochem Corp., San Diego Calif.).

Methods for glycosylation useful in combination with the selective deprotection methods provided herein are known in the art. Additional detail for such methods can be found in Davis B. G. (2002) Synthesis of Glycopeptides *Chem. Review* 102:579-601 and references cited therein.

In specific embodiments, the invention relates to selective sulfation of tyrosine residues in peptides or proteins.

The sulfation of tyrosine residues is a post-translational modification that occurs in all eukaryotes. This ubiquitous modification has been identified on many secretory proteins with diverse biological activities( ). Tyrosine O-sulfate [Tyr(SO$_3$H)] residues also are present in several biologically active peptides. (M. Farzan, T. Mirzabekov, P. Kolchinsky, R. Wyatt, M. Cayabyab, N. P Gerard, C. Gerard, J. Sodroski, H. Choe, Cell 1999, 96, 667-676; A. Leppanen, S. P. White, J. Helin, R. P. McEver, R. D. Cummings, J. Biol. Chem. 2000, 275, 39569-39578; E. G. Cormier, D. N. H. Tran, L. Yukhayeva, W. C. Olson, T. Dragic, J. Virol. 2001, 75, 5541-5549.) The biological significance of tyrosine sulfation, however, is known only for a few proteins in which sulfation appears to facilitate specific protein-protein interactions (e.g., J. W. Kehoe, C. R. Bertozzi, Chem. Biol. 2000, 7, 57-61.) Characterization of the molecular interactions of Tyr(SO$_3$H) has been hampered by lack of access to the necessary quantities of sulfated proteins and peptides. In a specific embodiment, this invention provides a method for the efficient production of sulfated peptides using a new protecting group strategy.

Although several strategies for the synthesis of sulfated peptides have been reported (Y. Kurano, T. Kimura, S. Sakakibara, J. Chem. Soc. Chem. Commun. 1987, 323-325; N. Fujii, S. Futaki, S. Funakoshi, K. Akaji, H. Morimoto, R. Doi, K. Inoue, M. Kogire, S. Sumi, M. Yun, T. Tobe, M. Aono, M. Matsuda, H. Narusawa, M. Moriga, H. Yajima, Chem. Pharm. Bull. 1988, 36, 3281-3291; K. Kitagawa, S. Futaki, T. Yagami, J. Synth. Org. Chem. Jpn. 1994, 52, 675-685), a general, efficient approach has not.

The primary obstacle encountered in the synthesis of sulfated peptides is the tendency of sulfotyrosine to undergo desulfation under acidic conditions. Sulfotyrosine-containing peptides decomposed rapidly in the presence of trifluoroacetic acid, the standard reagent used for side chain deprotection and cleavage from the solid supports employed in Fmoc-based solid-phase peptide synthesis (Fmoc-SPPS). In contrast, acid-sensitive substrates can be released from the 2-chlorotrityl (2-Clt) derivatized resin without significant decomposition. Indeed, sulfated peptides may be liberated from this support without significant accompanying desulfation (K. Kitagawa, C. Aida, H. Fujiwara, T. Yagami, S. Futaki, Tetrahedron Lett. 1997, 38, 599-602). While stepwise incorporation of FmocTyr(SO$_3$Na)OH (K. Kitagawa, C. Aida, H. Fujiwara, T. Yagami, S. Futaki, M. Kogire, J. Ida, K. Inoue, J. Org. Chem. 2001, 66, 1-10) appears to be an attractive method, couplings using this salt, and subsequent reactions to elongate the resulting peptide, are sluggish. Moreover, the syntheses of peptides containing multiple sulfotyrosine residues using this method was found to exhibit poor resin swelling and a need for extended coupling times.

In a preferred embodiment, this invention provides a post-synthetic sulfation strategy involving selective unmasking and sulfation of the desired tyrosine residues on a solid support. Incorporation of orthogonally protected tyrosine derivatives at the peptide assembly stage allows the synthesis of multiply sulfated peptides with various sulfation patterns. Additionally, a solid phase sulfation step avoids the complicated purification of partially protected, sulfated peptide intermediates, and in the case of poly-sulfated peptides, mixtures of different sulfation patterns. The use of excess reagents also could be used to drive the sulfation reaction to completion. In addition, with this strategy, both sulfated and unmodified peptides can be produced from the same peptide synthesis.

To implement this approach, a protecting group for the tyrosine phenol that is stable to the conditions used in Fmoc-SPPS (Solid Phase Protein Synthesis), but that can be unmasked selectively and quantitatively under mild conditions, was needed. Strongly acidic or basic conditions for protecting group removal were to be avoided. Additional benefit could be obtained if it was possible to circumvent the laborious process of cleavage and characterization of intermediates to confirm the deprotection reaction. A preferred protecting group would thus be removable under mild conditions and possess a characteristic spectroscopic signal by which the deprotection step could be monitored. The specific choice of protecting group was further constrained by a need to employ a group with orthogonal reactivity to both the chlorotrityl ester and the peptide.

An azide-bearing protecting group, exemplified by the azidomethylene (Azm) protecting group reported by B. Loubinoux (supra) for use in the synthesis of unstable phenols, was found to be suitable for application to the selective synthesis of sulfated peptides. The mild conditions required for azide reduction were found to release the phenol group without cleavage of the chlorotrityl ester bond or modification of oxidation-sensitive amino acid residues such as cysteine and methionine. (E. F. V. Scriven, K. Turnbull, Chem. Rev. 1988, 88, 297-368.)

The synthesis of the exemplary protected tyrosine (Fmoc-Tyr(OAzm)OH: see FIG. 1) proceeds from BocTyrOMe 2. Attempted alkylation of 2 with dibromomethane or bromo-chloromethane afforded only the dimeric tyrosine methylene acetal, even when high concentrations of the electrophile were employed. Alkylation with an alternate, bifunctional methylene equivalent, chloromethyl methylsulfide, proceeded in good yield (FIG. 2).

Initial screening of precedented methods for the selective activation of the O,S-acetal 3 (T. Benneche, K. Undheim, Acta Chem. Scand. B 1983, 37, 93-96; P. J. Garegg, In Advances in Carbohydrate Chemistry and Biochemistry 1997, 52, 179-205) failed to yield satisfactory results. For example, treatment of compound 3 with NCS in dichloromethane afforded only 48% yield of the desired compound, 4. Unsuccessful attempts to transform the O,S-acetal at high yield prompted a search for more reactive electrophilic activators. It was found that Lewis acid activation of N-chlorosuccinimide increased the consumption of starting material without compromising the stability of the product. Indeed, activation of the O,S-acetal with N-chlorosuccinimide in the presence of TMSCl provides the chloride 4 in good yield (FIG. 2). The labile intermediate 4 was purified by flash chromatography on deactivated silica gel, but not without some accompanying hydrolysis. A simple aqueous workup, however, provided 4 with little decomposition. The transformation of this material to the azide 5 proceeds in high yield (87% for 2 steps).

The azidomethylene group is not impervious to acidic conditions, a feature that complicates the synthesis of 1. Indeed, we were unable to achieve selective removal of the Boc carbamate using protic acids. TMSOTf was employed to selectively cleave the Boc group, (M. Sakaitani, Y. Ohfune, Tetrahedron Lett.,1985, 26, 5543-5546; A. J. Zhang, D. H. Russell, J. P. Zhu, K. Burgess, Tetrahedron Lett. 1998, 39, 7439-7442) and protected the resulting amino group by reaction with Fmoc-N-hydroxysuccinimide ester (J. Paladino, C. Guyard, C. Thurieau, J. L. Fauchere, Helv. Chim. Acta 1993, 76, 2465-2472.) Selective saponification of the methyl ester, the precursor to 1, provides the target compound, without loss of the Fmoc group, (T. R. Burke, M. S. Smyth, A. Otaka, P. P. Roller, Tetrahedron Lett. 1993, 34, 4125-4128) in excellent yield. The enantiopurity of this compound was confirmed by the synthesis of diastereomeric dipeptides, see the Examples.

Monomer 1 was used in a peptide synthesis strategy that was readily implemented (FIG. 3). Standard Fmoc-based solid-phase peptide synthesis was followed by unmasking of the desired phenols by cleavage of the Azm group using homogeneous conditions for azide reduction. (M. Bartra, P. Romea, F. Urpi, J. Vilarrasa, *Tetrahedron* 1990, 46, 587-594.)

Complete removal of the Azm moiety was confirmed by inspection of the infrared absorption spectrum for the strong, distinct azide stretch. The free phenolic hydroxyl groups were then sulfated by the action of $DMF.SO_3$ in a pyridine/DMF mixture. (Y. Matsubayashi, H. Hanai, O. Hara, Y. Sakagami, Biochem. Biophys. Res. Commun. 1996, 225, 209-214.)

In the exemplary synthetic strategy, benzyl side-chain protecting groups were used for other tyrosine residues, serine, threonine, aspartic acid and glutamic acid residues, necessitating a two-step cleavage/deprotection protocol. Cleavage from the acid labile 2-Clt resin under conditions compatible with the labile sulfate esters was followed by routine hydrogenolysis of the benzyl groups.

Application of the method of the invention was exemplified by synthesis of a sequence derived from PSGL-1, a sulfated glycoprotein. PSGL-1 has been shown to be the relevant ligand for P-selectin. (D. Sako, X. J. Chang, K. M. Barone, G. Vachino, H. M. White, G. Shaw, G. M. Veldman, K. M. Bean, T. J. Ahem, B. Furie, D. A. Cumming, G. R. Larsen, Cell, 1993, 75, 1179-1186.) Significantly, a sulfated epitope at the N-terminus of PSGL-1 is crucial for binding (a; D. Sako, K. M. Comess, K. M. Barone, R. T. Camphausen, D. A. Cumming, G. D. Shaw, Cell 1995, 83, 323-331; b) T. Pouyani, B. Seed, Cell, 1995, 83, 333-343. The peptides related to this epitope were to be synthesized. For syntheses of other sulfated peptides derived from PSGL-1, see: a) A. Leppanen, P. Mehta, Y. B. Ouyang, T. Z. Ju, J. Helin, K. L. Moore, I. van Die, W. M. Canfield, R. P. McEver, R. D. Cummings, J. Biol. Chem. 1999, 274, 24838; b) K. M. Koeller, M. E. B. Smith, R. F. Huang, C. H. Wong, J. Am. Chem. Soc. 2000, 122, 4241-2; c) P. Durieux, J. Femandez-Carneado, G. Tuchscherer, Tetrahedron Lett. 2001, 42, 2297-2299.

Figure 4B:
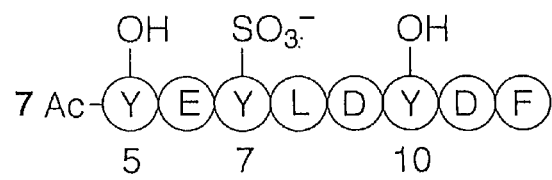

A peptide of sequence corresponding to residues 5-12 of mature PSGL-1 that contains all three putative sulfated tyrosine residues was synthesized. To demonstrate the flexibility of the inventive strategy, the fully sulfated octapeptide and a monosulfated octapeptide 7 (FIG. 4) were synthesized. Synthesis of the precursor to the tri-sulfated sequence 6 via automated continuous flow Fmoc-based chemistry proceeded smoothly. Amide bond formation with the inventive monomer building block proceeds with efficiency similar to that observed with other amino acid monomers; no special reagents or conditions were required. After the post-synthetic operations of Azm cleavage, sulfation, resin cleavage, and benzyl group hydrogenolysis, the desired peptide 6 was isolated in 27% yield after HPLC purification. Importantly, no desulfated peptide was observed in either the MALDI- TOF mass spectrum (prior to HPLC) or during HPLC purification. Synthesis of the monosulfated peptide 7 proceeded somewhat less efficiently, yielding several apparent deletion peptides in addition to the desired product. Still, after HPLC purification, the target peptide 7 was isolated in 5% overall yield based on resin loading. No desulfated peptide was detected.

The methods, protected monomers and kits of this invention can generally be employed for the synthesis of side-chain modified peptides and proteins and particularly for peptides and proteins modified at side-chain hydroxyl groups, including those of Try, Ser, Trp residues. The methods, protected monomers and kits of this invention can be employed alone or in combination with art-known methods and reagents for introduction of various side-chain modifications include sulfation, phosphorylation and glycosylation. The methods, protected monomers and kits can generally be employed in the synthesis of peptides or proteins of a selected specific structure. Furthermore, the methods, protected monomers and kits of the invention can be employed, in combination with art-known methods, in the synthesis of libraries of peptides having variations in number, type and position of side-chain modification. The methods, protected monomers and kits of the invention can, for example, be employed in the synthesis of combinatorial libraries comprising a plurality of peptides with varying structure and typically a combinatorial library containing a very large number of peptide or protein variations. Such libraries are useful in screening for variation in biological activity.

The invention is further described and illustrated in the following non-limiting examples.

THE EXAMPLES

Example 1

A: General Methods

All reactions were run in flame dried glassware under an inert atmosphere of nitrogen or argon and monitored by thin-layer chromatography (TLC). Reaction temperatures were monitored via external bath temperature. All materials obtained from commercial suppliers were used as received, unless otherwise noted. Anhydrous reaction solvents were distilled as follows: tetrahydrofuran and benzene from sodium/benzophenone ketyl; methylene chloride, triethylamine and pyridine from calcium hydride. DMF was rendered amine-free by treatment with Dowex 50WX8-200 cation exchange resin, H$^+$ form, 1 g/L. N-Chlorosuccinimide was recrystallized from benzene and residual solvent was removed under high vacuum (<0.1 torr). N-Bromosuccinimide was recrystallized from H$_2$O and the crystalline material dried over P$_2$O$_5$, under high vacuum (<0.1 torr). N-Iodosuccinimide was recrystallized from dioxane/CCl$_4$, dried under high vacuum and stored in the dark. Tetrabutyl ammonium azide was prepared by the method of Brändström et. al. (1974) "The Use of Tetrabutylammonium Azide in the Curtius Rearrangement," *Acta Chem. Scand.* B 28, 699-701 followed by azeotropic removal of residual moisture with pyridine and storage over P$_2$O$_5$.

HPLC was performed on Spectra-Physics UV2000 instrument using ultraviolet absorption at 220 nm and/or 254 nm for analyte detection. Samples were eluted on reverse phase C18 columns from Alltech (Econosil L=250 mm, ID=22 mm 10 □particle size) or Vydac (L=220 mm, ID=5 mm, 10 □particle size).

Infrared spectra were recorded on a Mattson Polaris FT-IR spectrometer and are reported in wavenumbers (cm$^{-1}$).

$^1$H and $^{13}$C NMR spectra were recorded on a Bruker AC-300 spectrometer or Varian Unity 500 spectrometer, and are referenced to internal standards (CHCl$_3$: $^1$H:

δ 7.24, $^{13}$C: δ 77.0; CH$_3$OH: $^1$H: δ 3.31, $^{13}$C: 49.15). $^1$H-$^1$H couplings are interpreted as first order. Peak multiplicity is reported as: singlet (s), doublet (d), triplet (t), quartet (q), multiplet (m), broad (br), and apparent (ap).

Analytical thin layer chromatography (TLC) was carried out on E. Merck (Darmstadt) TLC plates pre-coated with silica gel 60 F$_{254}$ (250μ layer thickness). Analyte visualization was accomplished using a UV lamp, and charring with at least one of the following solutions: a p-anisaldehyde stain (18 mLp-anisaldehyde, 7.5 mL glacial acetic acid, 25 mL conc. H$_2$SO$_4$, 675 mL absolute EtOH), ninhydrin solution (200 mg ninhydrin, 95 mL n-butanol, 5 mL 10% AcOH), potassium permanganate solution (3 g KMnO$_4$, 20 g K$_2$CO$_3$, 5 mL 5% aqueous NaOH, 300 mL H$_2$O). Flash chromatography was performed on Scientific Adsorbents Incorporated silica gel (32-63 μM, 60 Å pore size) using distilled reagent grade hexanes and ACS grade ethyl acetate, methanol and chloroform. The term, "concentrated in vacuo" refers to the removal of solvents and other volatile materials using a rotary evaporator at water aspirator pressure (<20 torr), followed by residual solvent removal at high vacuum (<0.1 torr). The term, "high vacuum," refers to vacuum achieved by a mechanical belt-drive oil pump.

All yields are reported as the average of three independent trials with the exception of the transformation of compound 271 to 270 (two trials) and peptide syntheses (one trial each). This averaging accounts for the discrepancy in yields reported in the below, representative procedures and in the text.

B. Detailed Synthetic Procedures

BocTyr(MTM)OMe:

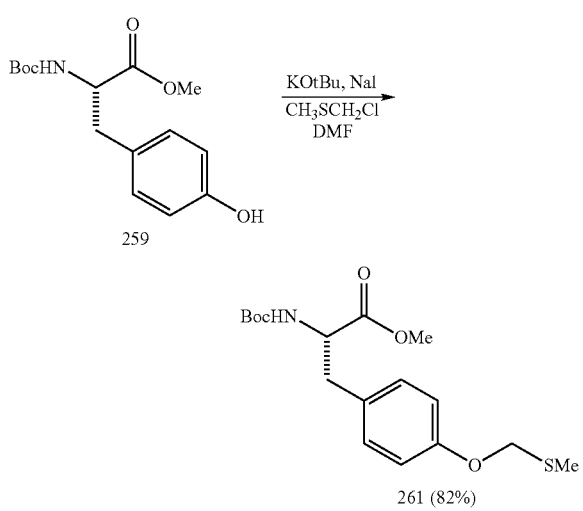

To a solution of BocTyrOMe (4.05 g, 13.7 mmol) and NaI (206 mg, 1.37 mmol) in DMF (30 mL) chilled via an external ice bath was added a THF (15 mL) solution of potassium t-butoxide (1.73 g, 15.1 mmol). To the resultant phenoxide (clear green solution) chloromethyl methyl sulfide (1.33 mL, 15.1 mmol) was added slowly. The reaction was allowed to warm gradually to room temperature. After 4.5 h, the reaction was cloudy and TLC analysis (4:1 hexanes/EtOAc) indicated complete consumption of starting material. The reaction mixture was diluted with EtOAc (60 mL) and washed with $H_2O$ (1×45 mL), aqueous citric acid solution (5%, 1×45 mL) and brine (1×45 mL). The aqueous washing were pooled and washed with EtOAc (2×60 mL). The combined organic extracts were pooled and dried over $MgSO_4$. The $MgSO_4$ was removed by filtration and volatiles removed in vacuo. The residue was purified by flash column chromatography (silica, gradient elution 4:1 hexanes/EtOAc to 2:1 hexanes/EtOAc) to afford a clear syrup on concentration 261 (3.99 g, 81%). $R_f$=0.44 (4:1, hexanes/EtOAc); IR (Neat): 3368, 1744, 1714, 1510 $cm^{-1}$; $^1H$ NMR (300 MHz, $CDCl_3$): δ 7.02-6.81(AA'BB', J=9.5, 4H), 5.06 (s, 2H), 4.99 (d, J=5.4, 1H), 4.49 (q, J=5.8, 1H), 3.66 (s, 3H), 2.18 (s, 3H), 1.36 (s, 9H); $^{13}C$ NMR (75 MHz, CDC1y): δ 172.2, 156.0, 130.3, 129.1, 116.0, 72.3, 54.4, 52.2, 37.5, 28.3, 14.4; LRMS (ESI): m/z 378 [M+Na$^+$ calc'd for $C_{17}H_{25}NO_5S$ 378.1]

BocTyr(CH$_2$)Cl:

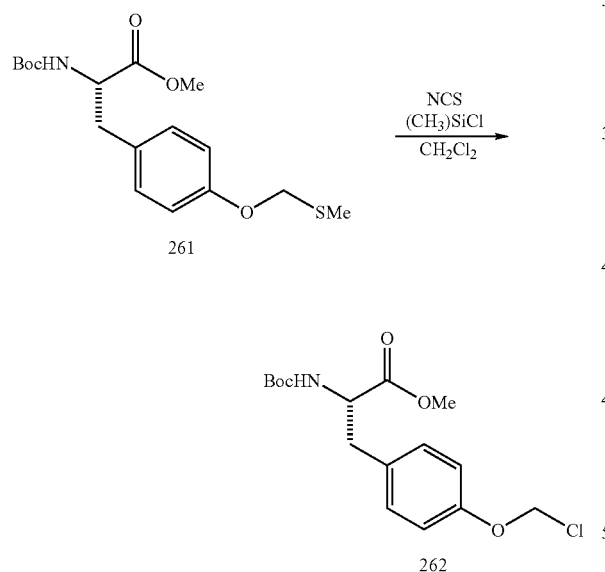

The O,S-acetal 261 (287 mg, 0.81 mmol) was dissolved in dichloromethane (3.0 mL), and solid NCS (119 mg, 0.89 mmol) was added. The reaction was allowed to stir for 2.5 h, then trimethylsilyl chloride (0.11 mL, 0.89 mmol) was added. After an additional 2 hours, the crude reaction mixture was loaded directly on to a flash silica gel column. Elution with 5:1 hexanes/EtOAc and drying in vacuo provided the compound as a clear oil in pure form for characterization. The compound 262 was crystallized to yield white plates under high vacuum for 10 h (202 mg, 73%). The mass balance was recovered as BocTyrOMe after elution with EtOAc. $R_f$=0.40 (4:1, hexanes/EtOAc); $^1H$ NMR (300 MHz, $CDCl_3$): δ 7.10-6.98 (AA'BB', J=8.8 Hz, 4H), 5.84 (s, 2H), 4.98 (d, J=7.7 Hz, 1H), 4.53 (q, J=7.8 Hz, 1H), 3.68 (s, 3H), 3.05-2.95 (m, 2H), 1.38 (s, 9H); $^{13}C$ NMR (75 MHz, $CDCl_3$): δ 172.1, 154.6, 130.4, 116.1, 54.3, 52.1, 37.4, 28.1; LRMS (MALDI, α-cyano-4-hydroxycinnamic acid matrix, positive ion mode): m/z 368.2, 366.1, 318.2 [calc'd M+Na$^+$ for $C_{16}H_{22}ClNO_5$ 366.11; M+Na$^+$ for $C_{15}H_{21}NO_5$ 318.13]

BocTyr(Azm)OMe:

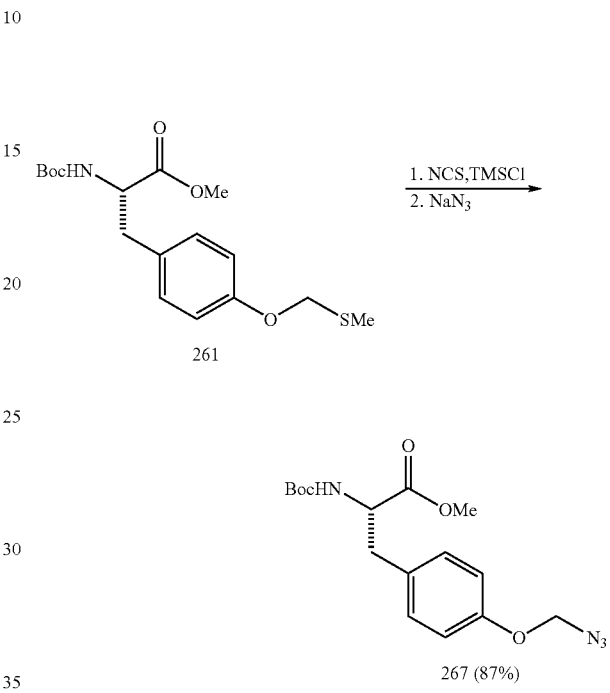

The O,S-acetal 261 (4.28 g) was dissolved in $CH_2Cl_2$ (35 mL) and solid N-chlorosuccinimide (1.76 g) was added. The reaction was allowed to stir at room temperature for 4 h. Trimethylsilyl chloride (1.68 mL) was then added slowly. After an additional 6 h, the reaction was diluted with $CHCl_3$ (30 mL) and saturated $NaHCO_3$ solution (60 mL) was added. The organic layer was separated and the aqueous fraction was extracted with $CHCl_3$ (2×60 mL). The combined organic extracts were concentrated via rotary evaporation and the residue dissolved in DMF (15 mL). Sodium azide (1.2 g, 18.5 mmol) was dissolved in $H_2O$ (15 mL) and added to the solution of crude tyrosyl chloride. This reaction was allowed to stir for 5 h at room temperature. The reaction was then diluted with saturated $NaHCO_3$ solution (15 mL) and washed with EtOAc (3×30 mL). The combined organic extracts were dried ($MgSO_4$) concentrated in vacuo, and the residue subjected to flash column chromatography (silica, gradient elution 4:1 hexanes/EtOAc to 2:1 hexanes/EtOAc). After removal of volatiles, azidomethylene 267 was isolated as a clear oil (3.64 g, 87%). $R_f$=0.41 (4:1 hexanes/EtOAc); IR (Neat): 2132, 2110 $cm^{-1}$; $^1H$ NMR (300 MHz, $CDCl_3$): δ 7.08-6.90 (AA'BB', J=8.5 Hz, 4 H), 5.13 (s, 2H), 4.95 (d, J=6.7 Hz, 1H), 4.55 (d, J=6.7 Hz 1H), 3.71 (s, 3H), 3.0 (m, 2H), 1.41 (s, 9H); $^{13}C$ NMR (75 MHz, $CDCl_3$): δ 172.1, 155.4, 130.3, 115.8, 79.6, 54.3, 51.9, 37.2, 28.0; LRMS (FAB): m/z 373.1 [M+Na$^+$ calc'd for $C_{16}H_{22}N_4O_5$ 373.2]

FmocTyr(Azm)OMe:

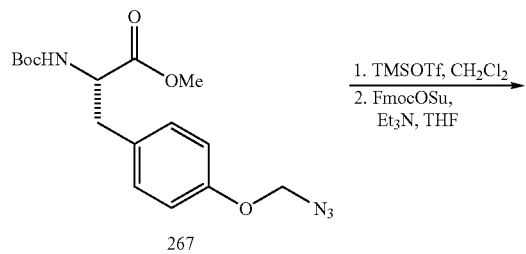

267

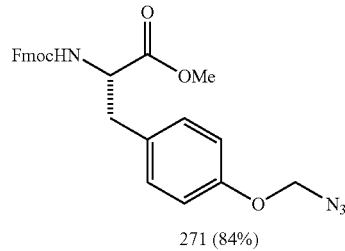

271 (84%)

Boc protected compound 267 (769 mg, 2.19 mmol) was dissolved in CH₂Cl₂ and cooled with an external ice bath. TMSOTf (0.79 mL, 4.4 mmol) was added dropwise. TLC analysis (4:1 Hexanes/EtOAc) indicated complete consumption of starting material after less than 10 min. 5% aqueous Na₂CO₃ was added (15 mL), followed by EtOAc (15 mL). The organic layer was separated and the aqueous phase extracted with EtOAc (3×15 mL). Volatiles were removed in vacuo and the residue was taken up in THF (7 mL). Triethylamine (0.91 mL, 6.6 mmol) was added, followed by solid FmocOSu (814 mg, 2.4 mmol). The reaction was left to stir for 3.5 h during which time a white precipitate formed. The reaction was diluted with CHCl₃ (15 mL) and washed with H₂O, 5% citric acid solution, and brine (15 mL each). The combined aqueous washings were extracted with CHCl₃ (4×15 mL). The pooled organic extracts were dried over MgSO₄ and filtered. The solvent was reduced to ca. 5 mL via rotary evaporation and loaded directly on a silica gel column. Flash chromatography (2:1 hexanes/EtOAc) yielded the compound 271 as a crystalline white solid (870 mg, 84%). Ry=0.36 (2:1 hexanes/EtOAc); ¹H NMR (300 MHz, CDCl₃): δ 7.76-7.74 (d, J=7.7 Hz, 2H, 7.57-7.53 (m, 2H), 7.41-7.36 (t, J=7.1 Hz, 2H), 7.36-7.23 (t, J=7.3 Hz, 2H), 7.02-6.88 (AA'BB', J=7.4 Hz, 4H), 5.28 (d, J=8.1 Hz, 1H), 5.09 (s, 2H), 4.63 (dd, J=7.0, J=10.6, 1H), 4.44 (dd, J=7.0, J=10.6, 1H), 4.16 (t, J=7.0, 1H), 3.71 (s, 3H), 3.13-2.99 (m, 2H); ¹³C NMR (75 MHz, CDCl₃): δ 171.7, 155.6, 143.7, 141.2, 130.4, 129.8, 127.6, 126.9, 126.8, 124.9, 119.9, 115.9, 79.6, 66.7, 54.7, 52.2, 47.0, 37.7; LRMS (ESI): m/z 495.1 [M+Na⁺ calc'd for C₂₆H₂₄N₄O₅ 495.16]

BocTyr(Azm)OH:

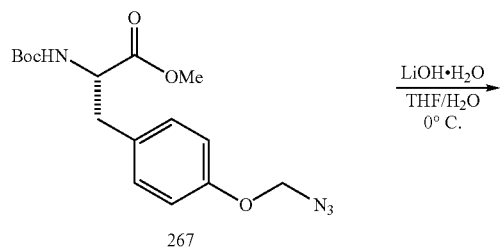

267

-continued

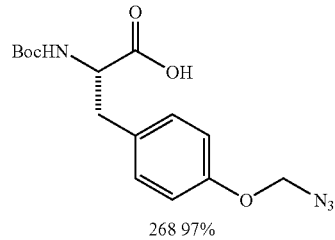

268 97%

Methyl ester 267 (622 mg, 1.78 mmol) was dissolved in THF (5 mL) and cooled with an external ice bath. LiOH.H₂O (224 mg, 5.34 mmol) was dissolved in H₂O (5 mL) and chilled in the ice bath. The LiOH solution was then added to the methyl ester in one aliquot. After stirring at 0° C. for 2 h TLC analysis (4:1, hexanes/EtOAc) indicated complete consumption of starting material. The reaction was diluted with 5% aqueous citric acid solution (20 mL), yielding an apparent pH of 3 (pH paper). The aqueous solution was extracted with EtOAc (4×20 mL). The combined organic extracts were pooled and dried over MgSO₄. Filtration and removal of volatiles in vacuo provided 268 as a white foam suitably pure (according to TLC, ¹H NMR) for analytical characterization (584 mg, 97%). ¹H NMR (300 MHz, CDCl₃): δ 8.75 (br s, 1H), 7.12-6.90 (AA'BB', J=6.9 Hz, 4H), 6.45 (m, minor rotamer NH) 4.96 (d, 7.7 Hz, major rotamer NH) 4.55 (m, major rotamer αH, 0.61/1H), 4.33 (m, minor rotamer αH, 0.38/1H), 2.95-2.80 (m, major rotamer, β2H), 1.40 (s, major rotamer, t-Bu), 1.29 (s, minor rotamer, t-Bu).

FmocTyr(Azm)OH:

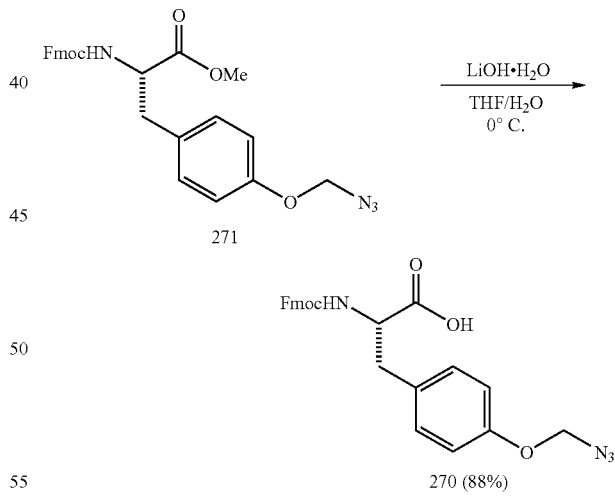

271

270 (88%)

Methyl ester 271 (339 mg, 0.72 mmol) was dissolved in THF (7 mL) and cooled to 0° C. with an external ice bath. LiOH.H₂O (60 mg, 1.4 mmol) was dissolved in H₂O (7 mL) and added dropwise over 10 minutes to the chilled solution of methyl ester. After an additional 25 min the starting material was completely consumed as judged by analytical TLC (2:1 hexanes/EtOAc). The pH was then adjusted to ca. 3 by adding 0.3 M aqueous HCl. The cloudy aqueous solution was extracted with EtOAc (4×15 mL). The organic extracts were pooled, dried over MgSO₄, filtered and concentrated in vacuo. Flash silica gel chromatography (10% MeOH/CHCl$_3$) provides 270 as a white solid after drying in vacuo (292 mg, 89%). $^1$H NMR (300 MHz, CDCl$_3$): δ 10.05 (br s, 1H), 7.78 (d, J=7.7 Hz, 2H), 7.59-7.52 (m, 2H), 7.41 (t, J=7.4 Hz, 2H), 7.32 (t, J=7.4 Hz, 2H), 7.09-6.90 (AA'BB', J=6.9 Hz, 4H), 6.20 (m, minor rotamer NH), 5.43 (d, J=8.1 Hz, major rotamer NH), 5.08 (s, 2H), 4.67 (q, J=6.6, 1H), 4.52-4.46 (m, 1H), 4.40-4.34 (m, 1H), 4.23-4.17 (m, 1H), 3.23-3.05 (m, major rotamer βH), 2.98-2.80 (m, minor rotamer βH); $^{13}$C NMR (75 MHz, CDCl$_3$): δ 155.4, 147.8, 143.3, 140.9, 130.2, 127.4, 126.7, 126, 124.6, 79.3, 66.7, 46.7, 36.5; LRMS (ESI): m/z 457.1, 235.1 [MH calc'd for C$_{25}$H$_{22}$O$_5$N$_4$ 457.15; MH calc'd for C$_{25}$H$_{22}$O$_5$N$_4$—C$_{15}$H$_{11}$O$_2$ 235.1].

FmocTyr(Azm)OH, Method B:

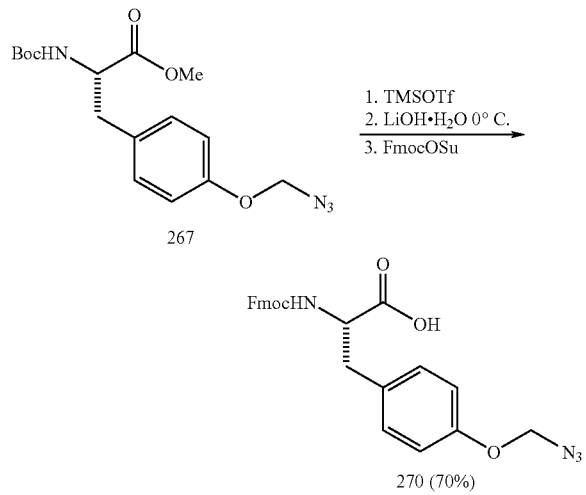

Boc Tyr(Azm)OMe 267 (766 mg, 2.19 mmol) was dissolved in CH$_2$Cl$_2$ (10 mL and cooled with an external ice bath. Trimethylsilyl triflate (0.79 mL, 4.4 mmol) was added dropwise over 3 minutes. After an additional 15 minutes, TLC analysis (5:1, hexanes/EtOAc) indicated complete consumption of starting material. Aqueous Na$_2$CO$_3$ solution (5%, 25 mL) was added, followed by 10 mL CHCl$_3$. The two phases were separated and the aqueous phase washed with EtOAc (4×25 mL). The combined organic extracts were dried (MgSO$_4$) and concentrated to give 2.1 g of an oil. This crude material was dissolved in THF (10 mL) and chilled via an external ice bath. A chilled solution of LiOH.H$_2$O (276 mg, 6.57 mmol) in H$_2$O (10 mL) was added. After 2 hours acetic acid (2.5 eq) was added and the ice bath was removed. Solid FmocOSu (740 mg, 2.19 mmol) was added, and this mixture was allowed to stir for 2 hours. The bulk of the THF was then removed via rotary evaporation and triethylamine (1 mL) was added. The crude aqueous mixture was filtered through a medium sintered glass frit and the solid washed with H$_2$O (3×15 mL). The combined aqueous mixture was acidified to an apparent pH of 2 (pH paper) with 1 N HCl and washed with EtOAc (4×60 mL). The combined organic extracts were concentrated and the residue purified by flash column chromatography (silica, gradient elution 95:5 CHCl$_3$/MeOH to 80:20 CHCl$_3$/MeOH). Drying in vacuo yields 270 as an off-white, chalky solid (678 mg, 1.53 mmol, 68%). Analytical data (TLC, $^1$HNMR, $^{13}$CNMR, LRMS) same as above.

Attachment of the C-Terminal Amino Acid to 2-Chlorotrityl Chloride Resin:

Amino acid is suspended in dichloromethane (DCM, 10 mL per gram of resin) and dimethylformamide (DMF) is added dropwise until the amino acid dissolves. 1.1 equivalents of diisopropylethylamine should be used relative to the total mmoles amino acid plus mmoles chloride. The amino acid is added to the resin along with ⅓ the total amount of diisopropylethylamine. After stirring with a small stir bar for five minutes the rest of the base is added, and the mixture is stirred for 1 hour. After 1 hour, 1 mL of methanol is added to cap the resin. The resin slurry is then transferred to a fritted funnel and rinsed with DCM (3×), DMF (2×), iPrOH (2×), DMF (2×), iPrOH (2×), MeOH (2×), and Et$_2$O (2×). Solvent volume for all washes is 8 mL per gram of resin.

The stability of the carboxylate-chlorotrityl bond is enhanced by deblocking of the α-amino group. Thus, the Fmoc group is cleaved by rinsing of the resin with 10% piperidine/CH$_2$Cl$_2$ (2×), followed by 20% piperidine/DMF for 20 minutes. The resin is agitated via sparging with nitrogen gas during this reaction. At the conclusion of the Fmoc cleavage the resin is rinsed, DCM (3×), DMF (2×), iPrOH (2×), DMF (2×), iPrOH (2×), MeOH (2×), and Et$_2$O (2×). Solvent volume for all washes is 8 mL per gram of resin. The resin is then dried under high vacuum and stored at sub-zero temperatures. In general, superior loadings are achieved using this protocol relative to commercially available, pre-loaded resins.

Peptide Synthesis:

Synthesis using FmocTyr(Azm)OH for the introduction of sulfotyrosine residues was carried out on 25 μM scale using an automated synthesizer (Applied Biosystems Model 432A "Synergy"). Standard techniques were used (Fields, G. B., and Noble, R. L. (1990) Solid-Phase Peptide-Synthesis Utilizing 9-Fluorenylmethoxycarbonyl Amino-Acids, International Journal of Peptide and Protein Research 35, 161-214; Merrifield, R. B. (1963) Solid Phase peptide Synthesis I, The synthesis of a Tetrapeptide, Journal of the American Chemical Society 85, 7129-7133.) The first amino acid was attached as above or the pre-loaded resins were purchased from Advanced Chemtech (Louisville, Ky.). Carboxylic and alcoholic side chains were protected with benzyl groups. Each synthesis cycle is initiated with the cleavage of the Fmoc group from the α-amino group, using 20% piperidine in DMF. Three equivalents (75 μmol) of the amino acid to be coupled is dissolved in DMF and added to the resin cartridge with HBTU (2-(1H-benzotriazol-1-yl)-1,1,3,3 tetramethyluronium hexafluorophosphate) and HOBt (N-hydroxybenzotriazole). The reaction cartridge is subjected to continuous flow conditions during each reaction. Following the coupling of the final amino acid, the peptide-resin cartridge is removed from the synthesizer. All subsequent manipulations of the peptide-resin are performed manually. Subsequent reactions are agitated by the "double syringe" method. Briefly, a luer lock syringe is attached to each end of the peptide synthesis cartridge and the syringes are moved reciprocally and in tandem to agitate the reaction.

Fmoc-Cleavage:

The resin-bound peptide is flushed with 5% piperidine/CH$_2$Cl$_2$ followed by treatment with 20% piperidine/DMF for 20 min. The piperidine solution is removed, and the resin rinsed [DCM (3×), DMF (2×), iPrOH (2×), DMF (2×)].

Acetylation:

The terminal amino group is acetylated prior to further synthetic manipulations. The peptide synthesis cartridge (PSC) is flushed with inert gas and rinsed with DMF (1 mL), 2:1 pyridine/Ac$_2$O (1 mL) is then added and the acetylation reaction agitated via the double syringe method. After three hours the resin is rinsed with 2:1 pyridine/Ac$_2$O (1 mL), and alternately with DMF, MeOH, CH$_2$Cl$_2$, Et$_2$O (3×1 mL each). Amine capping is confirmed by the Kaiser test (Kaiser, E. (1970). Analytical Biochemistry 34, 595).

General Protocol for Azidomethylene Cleavage of Resin-Bound Peptides:

To a conical flask charged with anhydrous SnCl$_2$ (57 mg 0.3 mmol) is added THF (2 mL), PhSH (104 µL, 1.2 mmol) and Et$_3$N (170 µL, ca. 1.2 mmol). This mixture is stirred briefly under Ar. The dry resin (0.025 mmol peptide) is flushed with THF (3×0.5 mL) and 1 mL of the reducing cocktail is added to the PSC. The reaction is agitated via the double syringe method. After ca. 5 minutes the reducing mixture is removed from the PSC and the resin rinsed with THF. The remainder of the reducing cocktail is added and the resin is agitated for ca. 5 minutes. The reducing cocktail is then removed and the resin washed alternately with moist THF:Et$_3$N (9:1, 4×1 mL), CH$_2$Cl$_2$ (4×1 mL), MeOH (4×1 mL) and DMF (4×1 mL).

Sulfation:

The PSC is flushed with 4:1 DMF/pyridine (1 mL). DMF.SO$_3$ (115 mg, 0.75 mmol) is dissolved in 4:1 DMF/pyridine and the resultant solution added to the PSC. The sulfation reaction is agitated by the double syringe method. After eight hours the resin is rinsed with 4:1 DMF/pyridine (1 mL) and the sulfation repeated with fresh DMF.SO$_3$ for an additional eight hours. The resin is then washed alternately with 4:1 DMF/pyridine and methanol (3×1 mL), then DMF, CH$_2$Cl$_2$, Et$_2$O (3×1 mL each).

Cleavage of Sulfotyrosine Peptides from 2-Chlorotrityl Resin:

The resin is dried under vacuum for at least 2 h prior to attempting the cleavage reaction. The dried resin is transferred to a round bottom flask and placed in an ice bath. A solution of 7:2:1 CH$_2$Cl$_2$/TFE/AcOH is cooled in an ice bath. Cleavage solution (10 mL per gram of resin) is added and the slurry stirred with a magnetic stir bar for 1.5 h. The cleavage mixture is then filtered through a sintered glass frit and the resin rinsed with three additional volumes of cleavage solution. The filtrate is then concentrated via rotary evaporation at ca. 10° C. to ca. ⅓ of the original volume. 100 mM ammonium acetate buffer is added and the mixture lyophilized to dryness. The crude material is then subjected to HPLC purification.

AcYA: This dipeptide was synthesized manually using the double syringe method. Fmoc-L-Ala was attached to 2-Clt resin according to the standard procedure. Fmoc cleavage was followed by coupling of FmocTyr(Azm) (PyBop, DIPEA) according to the method of Castro et al. Fmoc cleavage and acetylation was followed by cleavage from the support. HPLC purification [Vydac C18, gradient elution: A=0.1% TFA/H$_2$O, B: CH$_3$CN/0.1% TFA 0-20% B/30 min t$_2$=26.76. Excision of the peaks and weighing on an analytical balance revealed relative peak size of 92.3:7.7 (84.6% ee). The synthesis of this dipeptide was repeated using Carpino's amide bond forming conditions (HATU, HOAt, collidine). All other steps were performed in the same way. This synthesis yielded material with a relative peak size of at least 95:5 (>90% ee).

$^1$H NMR (300 MHz, CD$_3$OD): δ 8.35 (d, J=6.5 Hz, amide NH), 7.10-6.69 (AB q, J=6.4 Hz, 4H), 4.58 (dd, J=4.3, J=5.0, 1H), 4.43-4.36 (m, 1H), 3.11-2.73 (m, 2H), 1.90 (s, 3H), 1.41 (d, J=7.5, 3H).

AcY-(D)-A: HPLC purification [Vydac C18, gradient elution: A=0.1% TFA/H$_2$O, B: CH$_3$CN/0.1% TFA 0-20% B/30 min t$_2$=21.4 min. Excision and weighing of the peaks gave a ratio of 92.4:7.6 (84.8% ee). The synthesis of this dipeptide was repeated, as above, using Carpino's amide bond forming conditions (HATU, HOAt, collidine). This synthesis yielded material with a relative peak size of at least 95:5 (>90% ee).

AcY$_S$EY$_S$LDY$_S$DF (SEQ ID NO 2): The peptide was synthesized on 0.025 mmol scale by standard coupling procedures. Commercially available pre-loaded resin (0.5 mmol/g) was used. The N-terminal Fmoc group was cleaved and the amino group acetylated. The azidomethylene group was cleaved in the usual way. Sulfation was performed as described above. Cleavage and lyophilization affords 28 mg of a white solid. HPLC purification [Alltech Econosil C18, one major peak: t$_2$=22.76 min, gradient system: CH$_3$CN/0.1 M aq. NH$_4$OAc 5%-75% in 40 min, 8 mL/min] affords 8 mg (27% based on resin loading, minus resin for characterization) of a flocculent white solid. IR (KBr): 1244 br, str, 1050 br, str; LRMS (MALDI, α-cyano-4-hydroxycinnamic acid matrix, negative ion mode): m/z 1138.3 [calc'd M−3SO$_4$+NH$_4^+$1138.48].

AcYEYLDYDF (SEQ ID NO 4): A fraction of the phenol-deprotected material (10 mg resin) from the synthesis of AcY$_S$EY$_S$LDY$_S$DF (SEQ ID NO 2) above was cleaved (yield 6 mg), dissolved in MeOH/H$_2$O (2 mL) and subjected to hydrogenation over Pearlman's catalyst (10 mg) for 12 h under an H$_2$ filled balloon. Filtration through pre-rinsed Celite (MeOH/H$_2$O, 1:1 eluant) afforded 3 mg crude material after lyophilization. LRMS (FAB α-cyano-4-hydroxycinnamic acid matrix, positive ion mode): m/z 1215.4 [calc'd MH+2Na$^+$1215.44].

AcYEY$_S$LDYDF (SEQ ID NO 3): The solid phase synthesis was performed according to the general procedures described above. Cleavage from the resin gave 17 mg of crude peptide. This material was subjected to hydrogenation over Pearlman's catalyst (20 mg) for 12 h under an H$_2$ filled balloon. Filtration through pre-rinsed Celite (H$_2$O eluant). This material was subjected to HPLC (Alltech Econosil C18) gave three major peaks, two of which appeared to be deletion peptides (by MALDI-MS, we were unable to assign a structure based on the mass spectra, however the peptides appeared to be sulfated, as judged by HPLC retention time). The longest retained peptide (t$_r$=33.48 min, gradient system: CH$_3$CN/0.1 M aq. NH$_4$OAc 5%-75% in 40 min, 8 mL/min] pooling of this HPLC fraction and lyophilization afforded the desired peptide as a fluffy white solid (4.6 mg, 5.2%) LRMS (MALDI, α-cyano-4-hydroxycinnamic acid matrix, negative ion mode): m/z 1170.4 [calc'd M−SO$_4^-$+NH$_4^+$ 1169.42]; (MALDI, 2,4,6-trihydroxyaceto-phenone, negative ion mode): m/z 1191.6 [calc'd M−SO$_3$+Na$^+$ for C$_{57}$H$_{68}$N$_8$O$_{22}$S 1191.41] IR (KBr): 1256 br, str, 1049 br, str.

ACY$_{Bn}$E$_{Bn}$YLD$_{Bn}$Y$_{Bn}$D$_{Bn}$F: After azidomethylene deprotection of the above peptide-resin a small portion was cleaved (8 mg resin) to yield ca. 2.5 mg of intermediate crude peptide. LRMS (FAB, α-cyano-4-hydroxycinnamic acid matrix, positive ion mode): m/z 1642.6 [calc'd MH+Na$^+$1642.69] Other lower molecular weight peaks were observed, but were not assignable.

Synthesis of Peptides by Stepwise Coupling of FmocTyr (SO$_3$Na)OH:

Syntheses incorporating FmocTyr(SO$_3$Na) in stepwise fashion were performed manually. Solvent volumes for the coupling steps and for washes are at least 10 mL per gram of resin. For coupling to non-sulfated tyrosine residues:

Amino acid (3 equivalents relative to loading capacity) is dissolved in one half of the total amount of NMP. PyBOP (3 equivalents relative to loading capacity) is dissolved in one quarter of the total amount of NMP. The resin is rinsed with one eighth of the total amount of NMP. Collidine (TMP, 9 equivalents relative to the loading capacity) is then added to the resin, followed by the amino acid solution and then the PyBOP solution. The resin is agitated with a nitrogen stream for 90 minutes, then all reagents are removed from the resin under vacuum. The resin is washed with NMP (4×) and MeOH(4×). Coupling completion is assessed using the Kaiser test.

Coupling of Sulfated Tyrosine Residues:

Amino acid (3 equivalents relative to loading capacity) is dissolved in one half of the total amount of NMP. HATU (3 equivalents relative to loading capacity) is dissolved in one quarter of the total amount of NMP. The resin is rinsed with one eighth of the total amount of NMP. HOAT 0.5M in NMP (1 equivalent relative to the loading capacity) is added to the resin, followed by collidine (TMP, 9 equivalents relative to the loading capacity), the amino acid solution and then the HATU solution. The resin is agitated with a nitrogen stream for 90 minutes, then all reagents are removed from the resin under vacuum. The resin is washed with NMP (4×) and MeOH(4×). Coupling is monitored using the Kaiser test.

Cleavage of Sulfated Peptides from Chlorotrityl Resin:

The resin is dried under high vacuum for two hours before the cleavage reaction is attempted. Dichloromethane/trifluoroethanol/acetic acid cleavage solution (7:2:1 v:v:v, 10 mL per gram of resin) is cooled to 0° C. and added to a flask containing dried resin in an ice bath. The mixture is stirred for 1.5 hours at 0° C. During this time the temperature does not exceed 5° C. At the end of the reaction time the free peptide is filtered into a flask. The resin is then washed with the same volume of cleavage solution (at 0° C.) used in the reaction. Both washes are combined and most of the solvent is evaporated on a rotary evaporator (water bath less than 10° C.). Ether (40 mL) is added to the residue, the peptide is pelletted on the centrifuge and the ether is decanted. This procedure is repeated for another ether wash (40 mL) and for an ethyl acetate/ether wash (1.5:1 v:v, 25 mL total). The peptide pellet is redissolved in methanol, transferred to a flask, and evaporated to an oil (rotary evaporator water bath less than 10° C.). The oil is redissolved in methanol and evaporated to remove acetic acid. The oil is then lyophilized twice from MQ water to remove any traces of acetic acid. After removal of acetic acid, the crude peptide is stored at −25° C. until HPLC purification.

L-Glutamic acid γ-benzyl-γ-allyl ester:

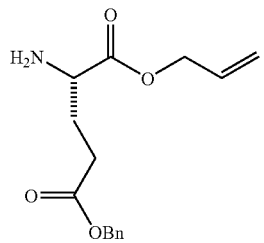

227

N-α-Fmoc-L-glutamic acid γ-benzyl ester-α-allyl ester was taken up in $CH_2Cl_2$/DMF (1:1, 20 mL) and piperidine (7.5 mL) was added neat. After 25 minutes TLC analysis (2:1 Hex/EtOAc) indicated complete consumption starting material. The volume was reduced to ca. 2 mL in vacuo, dry $Et_2O$ was added (30 mL) followed by concentrated HCl. A precipitate formed immediately and was filtered, washed with $Et_2O$ and dried. The free base was obtained by dissolution in $H_2O$, neutralization with aqueous $NaHCO_3$ solution, extraction with EtOAc and drying in vacuo. This material was suitably pure for the next step. Analytically pure material was obtained by flash silica gel chromatography (of the free base 20% MeOH—$CHCl_3$). $^1$H NMR (300 MHz, CDCl_y): δ 7.35 (a s, 5H), 5.96-5.87 (m, 1H), 5.36 (dd, J=1.5 Hz, J=7.1 Hz, 1H), 5.28 (dd, J=1.4 Hz, J=10.0 Hz, 1H), 5.13 (s, 2H), 4.62 (a d, J=5.7 Hz, 2H), 3.50 (dd, J=5.1, J=7.6 Hz, 1H), 2.53 (t, J=7.5, 2H), 2.18-1.84 (m, 2H).

$FmocY_SE_{Bn}OH$: Fmoc-L-glutamic acid γ-benzyl ester was attached to 2-Clt resin in the usual way. The resin loading was determined to be 0.75 mmol/g by quantitation of Fmoc cleavage. Resin (450 mg, 0.34 mmol) was subjected to the usual Fmoc cleavage conditions. FmocTyr ($SO_3Na$) was coupled using the general HATU-mediated coupling conditions described above [2×(450 mg, 0.7 mmol)] with an extended coupling time (5 h). Cleavage of the dipeptide from the resin using the general cleavage conditions afforded suitably pure dipeptide (yield 67%) as assayed by $^1$HNMR and analytical HPLC [gradient 25:75 $CH_3CN$/0.1 M aqueous $NH_4OAc$-75:25/30 min, at 3 mL/min; retention time: 24.7 min, Vydac C18]. $^1$H NMR (300 MHz, $CD_3OD$): δ 7.75 (d, J=7.4, 1H), 7.56-7.21 (m, 17H), 5.03 (d, J=2.6 Hz, 1H), 4.90 (s, 2H), 4.49 (aq, J=4.8 Hz, 1H), 4.32 (td, J=5.9, 2.6 Hz), 4.25-4.10 (m, 3H), 3.12-2.68 (m, 2H), 2.47-2.42 (m, 2H), 2.22-2.18 (m, 1H), 1.98-1.91 (m, 1H).

$FmocY_SE_{Bn}Y_SLD_{Bn}Y_SD_{Bn}F$: The stepwise procedure was employed as described above for the first six residues. The hexapeptide was α-amino deprotected as usual. The dipeptide, $FmocY_SE_{Bn}OH$ (2.3 equivalents), was then coupled to the support-bound hexapeptide using HATU and HOAt (5 h). Cleavage of the octapeptide was accomplished in the usual way. HPLC [Econosil C18, gradient 25:75 $CH_3CN$/0.1 M aqueous $NH_4OAc$-75:25/30-40 min at 8 mL/min; retention time: 25.4 min] (11% yield based on resin loading). $^1$HNMR (300 MHz, $CD_3OD$) is consistent with the structure.

$pEY_SLDYDF$ (SEQ ID NO 5): This peptide was generated in the attempted synthesis of $FmocY_SEY_SLDY_SDF$ (SEQ ID NO 2) via the stepwise protocol described above. HPLC purification of the product and analytical characterization revealed the pyroglutamate-terminated structure. A satisfactory mass spectrum was not obtained for this compound. However, 2-dimensional $^1$HNMR analysis (TOCSY, COSY) showed, unambiguously, this sequence. HPLC [Econosil C18, gradient 25:75 $CH_3CN$/0.1M aqueous $NH_4OAc$-75:25/30-40 min at 8 mL/min; retention time: 36.8 min].

Those of ordinary skill in the art will recognize that materials, methods and procedures, including among others: starting materials, reagents, solvents, resins, reaction conditions, side-chain protecting groups, α-amino protecting groups, and carboxyl protecting groups, other than those specifically disclosed herein can be employed in the practice of this invention without resort to undue experimentation. Functional equivalents of materials, methods and procedures employed in the examples herein are known in the art and are intended to be encompassed by this invention.

REFERENCES (1999). Genome sequence of the nematode *C. elegans*: A platform for investigating biology (vol 282, pg 2012, 1998). Science 285, 1493-1493.

Albericio, F. (2000). Orthogonal protecting groups for N alpha-amino and C-terminal carboxyl functions in solid-phase peptide synthesis. Biopolymers 55, 123-139.

Albericio, F., and Carpino, L. A. (1997). Coupling reagents and activation. In Solid-Phase Peptide Synthesis, Methods in Enzymology 201, pp. 104-126.

Albericio, F., Kneibcordonier, N., Biancalana, S., Gera, L., Masada, R. I., Hudson, D., and Barany, G. (1990). Preparation and Application of the 5-(4-(9-Fluorenylmethyloxycarbonyl)Aminomethyl-3,5-Dimethoxyphenoxy)Valeric Acid (Pal) Handle For the Solid-Phase Synthesis of C-Terminal Peptide Amides Under Mild Conditions. Journal of Organic Chemistry 55, 3730-3743.

Allaway, G. P., Davisbruno, K. L., Beaudry, G. A., Garcia, E. B., Wong, E. L., Ryder, A. M., Hasel, K. W., Gauduin, M. C., Koup, R. A., McDougal, J. S., and Maddon, P. J. (1995). Expression and Characterization of Cd4-Igg(2), a Novel Heterotetramer That Neutralizes Primary HIV Type-1 Isolates. Aids Research and Human Retroviruses 11, 533-539.

Anastasi, A., Bertaccini, G., and Erspamer, V. (1966). Pharmacological data on phyllokinin (brady-kinyl-isoleucyl-tyrosine O-sulphate) and bradykinyl-isoleucyl-tyrosine. British Journal of Pharmacology and Chemotherapy 125, 57-68.

Andersen, B. N., and Stadil, F. (1983). Sulfation of Gastrin in Zollinger-Ellison Sera—Evidence For Association Between Sulfation and Proteolytic Processing. Regulatory Peptides 6, 231-239.

Anderson, C. F., Record, M. T., Jr., (1982). Poly-electrolyte Theories and Their Application to DNA, Annual Review of Physical Chemistry 33, 191-222.

Andrews, D. W. (1991). International Journal of Peptide and Protein Research 38, 469.

Atherton, E., and Sheppard, R. C. (1989). Solid Phase Peptide Synthesis, A Practical Approach (Oxford: IRL Press at Oxford University Press).

Baeuerle, P. A., Lottspeich, F., and Huttner, W. B. (1988). Purification of Yolk Protein-2 of *Drosophila-Melanogaster* and Identification of Its Site of Tyrosine Sulfation. Journal of Biological Chemistry 263, 14925-14929.

Barlos, K., Gatos, D., Kallitsis, J., Papaphotiu, G., Sotiriu, P., Yao, W. Q., and Schafer, W. (1989). Synthesis of Protected Peptide-Fragments Using Substituted Triphenylmethyl Resins. Tetrahedron Letters 30, 3943-3946.

Barlos, K., Gatos, D., Kapolos, S., Papaphotiu, G., Schafer, W., and Yao, W. Q. (1989). Esterification of Partially Protected Peptide-Fragments With Resins—Utilization of 2-Chlorotritylchloride For Synthesis of Leu-15-Gastrin-I. Tetrahedron Letters 30, 3947-3950.

Barlos, K., Gatos, D., Kapolos, S., Poulos, C., Schafer, W., and Yao, W. Q. (1991). Application of 2-Chlorotrityl Resin in Solid-Phase Synthesis of (Leu(15))-Gastrin-I and Unsulfated Cholecystokinin Octapeptide—Selective 0-Deprotection of Tyrosine. International Journal of Peptide and Protein Research 38, 555-561.

Bartra, M., Romea, P., Urpi, F., and Vilarrasa, J. (1990). A Fast Procedure For the Reduction of Azides and Nitro-Compounds Based On the Reducing Ability of Sn(Sr)3-Species. Tetrahedron 46, 587-594.

Benneche, T., and Undheim, K. (1983). Synthesis of Alpha-Haloalkyl Aryl Ethers From O,S-Acetals. Acta Chemica Scandinavica Series B-Organic Chemistry and Biochemistry 37, 93-96.

Bennett, E. P., Hassan, H., Mandel, U., Mirgorodskaya, E., Roepstorff, P., Burchell, J., Taylor-Papadimitriou, J., Hollingsworth, M. A., Merkx, G., van Kessel, A. G., Eiberg, H., Steffensen, R., and Clausen, H. (1998). Cloning of a human UDP-N-acetyl-alpha-D-galactosamine: polypeptide N-acetylgalactosaminyltransferase that complements other GalNAc-transferases in complete O-glycosylation of the MUC1 tandem repeat. Journal of Biological Chemistry 273, 30472-30481.

Benz, H. (1994). The Role of Solid-Phase Fragment Condensation (SPFC) in Peptide-Synthesis. Synthesis-Stuttgart, 337-358.

Berg, E. L., Magnani, J., Warnock, R. A., Robinson, M. K., and Butcher, E. C. (1992). Comparison of L-Selectin and E-Selectin Ligand Specificities: L-Selectin can Bind the E-Selectin Ligands Sia)yl-Le" and Sialyl Le°. Biochemical and Biophysical Research Communications 184, 1048-1055.

Bevilacqua, M. P., and Nelson, R. M. (1993). Endothelial-Leukocyte Adhesion Molecules in Inflammation and Metastasis. Thrombosis and Haemostasis 70, 152-154.

Bing, Y. (1998). Monitoring the progress and the yield of solid phase organic reactions directly on resin supports. Accounts of Chemical Research 31, 621-630.

Binley, J. M., Sanders, R. W., Clas, B., Schuclke, N., Master, A., Guo, Y., Kajumo, F., Anselma, D. J., Maddon, P. J., Olson, W. C., and Moore, J. P. (2000). A recombinant human immunodeficiency virus type 1 envelope glycoprotein complex stabilized by an intermolecular disulfide bond between the gp 120 and gp41 subunits is an antigenic mimic of the trimeric virion-associated structure. Journal of Virology 74, 627-643.

Bird, M. I., Foster, M. R., Priest, R., and Malhotra, R. (1997). Selectins: physiological and pathophysiological roles. Biochemical Society Transactions 25, 1199-1206.

Blackburn, G. M., Eckstein, F., Kent, D. E., and Perree, T. D. (1985). Isopolar Vs Isosteric Phosphonate Analogs of Nucleotides. Nucleosides & Nucleotides 4, 165-167.

Bodanszky, M., Martinez, J., Priestley, G. P., Gardener, J. D., and Mutt, V. (1978). Cholecystokinin (pancreozymin) 0.4. Synthesis and properties of a biologically active analog of C-terminal heptapeptide with e-hydroxynorleucine sulfate replacing tyrosine sulfate. Journal of Medicinal Chemistry 21, 1030-1035.

Bose, A. K., Manhas, M. S., Vincent, J. E., Gala, K., and Fernandez, I. F. (1982). Studies On Lactams 0.65. N-Unsubstituted Beta-Lactams From Beta-Hydroxy-Alpha-Amino Acids—Facile Preparation of Intermediates For Isocephalosporins. Journal of Organic Chemistry 47, 4075-4081.

Brand, S. J., Andersen, B. N., and Rehfeld, J. F. (1984). Complete Tyrosine-0-Sulfation of Gastrin in Neonatal Rat Pancreas. Nature 309, 456-458.

Brand, S. J., Klarlund, J., Schwartz, T. W., and Rehfeld, J. F. (1984). Biosynthesis of Tyrosine 0-Sulfated Gastrins in Rat Antral Mucosa. Journal of Biological Chemistry 259, 3246-3252.

Brandstrom, A., Lamrn, B., and Palmertz, I. (1974). The Use of Tetrabutylammonium Azide in the Curtius Rearrangement. Acta Chem. Scand. B 28, 699-701.

Bundgaard, J. R., Vuust, J., and Rehfeld, J. F. (1997). New consensus features for tyrosine 0-sulfation determined by mutational analysis. Journal of Biological Chemistry 272, 21700-11705.

Bundgaard, J. R., Vuust, J., and Rehfeld, J. F. (1995). Tyrosine 0-Sulfation Promotes Proteolytic Processing of Progastrin. Embo Journal 14, 3073-3079.

Burke, T. R., Smyth, M. S., Otaka, A., and Roller, P. P. (1993). Synthesis of 4-Phosphono(Difluoromethyl)-D, L-Phenylalanine and N-Boc and N-Fmoc Derivatives Suitably Protected For Solid-Phase Synthesis of Nonhydrolyzable Phosphotyrosyl Peptide Analogs. Tetrahedron Letters 34, 4125-4128.

Carpino, L. A. (1987). The 9-Fluorenylmethyloxycarbonyl Family of Base-Sensitive Amino-Protecting Groups. Accounts of Chemical Research 20, 401-407.

Carpino, L. A., Elfaham, A., Minor, C. A., and Albericio, F. (1994). Advantageous Applications of Azabenzotriazole (Triazolopyridine)-Based Coupling Reagents to Solid-Phase Peptide-Synthesis. Journal of the Chemical Society-Chemical Communications, 201-203.

Carpino, L. A., and Han, G. Y. (1970). Journal of the American Chemical Society 92, 5748.

Carpino, L. A., Shroff, H., Triolo, S. A., Mansour, E. M. E., Wenschuh, H., and Albericio, F. (1993). The 2,2,4,6,7-Pentamethyldihydrobenzofuran-S-Sulfonyl Group (Pbf) As Arginine Side-Chain Protectant. Tetrahedron Letters 34,7829-7832.

Chan, W. C., and White, P. D. (2000). Fmoc solid phase peptide synthesis: a practical approach (Oxford: Oxford University Press).

Choe, H., Farzan, M., Konkel, M., Martin, K., Sun, Y., Marcon, L., Cayabyab, M., Berman, M., Dorf, M. E., Gerard, N., Gerard, C., and Sodroski, J. (1998). The orphan seven-transmembrane receptor Apj supports the entry of primary T-cell-line-tropic and dualtropic human immunodeficiency virus type 1. Journal of Virology 72, 6113-6118.

Choe, H., Farzan, M., Sun, Y., Sullivan, N., Rollins, B., Ponath, P. D., Wu, L. J., Mackay, C. R., LaRosa, G., Newman, W., Gerard, N., Gerard, C., and Sodroski, J. (1996). The beta-chemokine receptors CCR3 and CCR5 facilitate infection by primary HIV-1 isolates. Cell 85, 1135-1148.

Claverie, J. M. (2001). Gene number—What if there are only 30,000 human genes? Science 291, 1255-1257.

Cormier, E. G., Persuh, M., Thompson, D. A. D., Lin, S. W., Sakmar, T. P., Olson, W. C., and Dragic, T. (2000). Specific interaction of CCR5 amino-terminal domain peptides containing sulfotyrosines with HIV-1 envelope glycoprotein gp120. Proceedings of the National Academy of Sciences of the United States of America 97, 5762-5767.

Cormier, E. G., Tran, D. N. H., Yukhayeva, L., Olson, W. C., and Dragic, T. (2001). Mapping the determinants of the CCR5 amino-terminal sulfopeptide interaction with soluble human immunodeficiency virus type 1 gpl20-CD4 complexes. Journal of Virology 75, 5541-5549.

Coste, J., Lenguyen, D., and Castro, B. (1990). Pybop—a New Peptide Coupling Reagent Devoid of Toxic By-Product. Tetrahedron Letters 31, 205-208.

Crockett-Torabi, E. (1998). Selectins and mechanisms of signal transduction. Journal of Leukocyte Biology 63, 1-14.

Curtius (1912). Chem. Ber. 45, 1086.

Debont, H. B. A., Vanboom, J. H., and Liskamp, R. M. J. (1990). Automatic Synthesis of Phosphopeptides By Phosphorylation On the Solid-Phase. Tetrahedron Letters 31, 2497-2500.

Deng, H. K., Unutmaz, D., KewalRamani, V. N., and Littman, D. R. (1997). Expression cloning of new receptors used by simian and human immunodeficiency viruses. Nature 388, 296-300.

Desmarais, S., Jia, Z. C., and Ramachandran, C. (1998). Inhibition of protein tyrosine phosphatases FIPIB and CD45 by sulfotyrosyl peptides. Archives of Biochemistry and Biophysics 354, 225-231.

Dong, J. F., Li, C. Q., and Lopez, J. A. (1994). Tyrosine Sulfation of the Glycoprotein Ib-Ix Complex—Identification of Sulfated Residues and Effect On Ligand-Binding. Biochemistry 33, 13946-13953.

Doranz, B. J., Rucker, J., Yi, Y. J., Smyth, R. J., Samson, M., Peiper, S. C., Parmentier, M., Collman, R. G., and Doms, R. W. (1996). A dual-tropic primary HIV-1 isolate that uses fusin and the beta-chemokine receptors CKR-S, CKR-3, and CKR-2b as fusion cofactors. Cell 85, 1 149-1158.

Dorman, L. C., Nelson, D. A., and Chow, R. C. L. (1972). In Progress in Peptide Research, S. Lande, ed. (New York: Gordon and Breach), pp. 65-68.

Dorner, B., Steinauer, R., and White, P. (1999). Solid-phase organic chemistry: Linkers and functionalized solid supports. Chimia 53, 11-17.

Dorner, B., and White, P. (2000). Synthesis Notes. In Novabiochem Catalog (San Diego: Calbiochem-Novabiochem Corp), pp. P33.

Drickamer, K. (1993). Ca-°-dependent carbohydrate-recognition domains in animal proteins. Current Opinion in Structural Biology 3, 393-400.

Faham, S., Hileman, R. E., Fromm, J. R., Linhardt, R. J., and Rees, D. C. (1996). Heparin Structure and Interactions with Basic Fibroblast Growth Factor. Science 271, 1116-20.

Farzan, M., Choe, H., Martin, K., Marcon, L., Hofmann, W., Karlsson, G., Sun, Y., Barrett, P., Marchand, N., Sullivan, N., Gerard, N., Gerard, C., and Sodroski, J. (1997). Two orphan seven-transmembrane segment receptors which are expressed in CD4-positive cells support simian immunodeficiency virus infection. Journal of Experimental Medicine 186, 405-411.

Farzan, M., Mirzabekov, T., Kolchinsky, P., Wyatt, R., Cayabyab, M., Gerard, N. P., Gerard, C., Sodroski, J., and Choe, H. (1999). Tyrosine sulfation of the amino terminus of CCR5 facilitates HIV-1 entry. Cell 96, 667-676.

Farzan, M., Vasilieva, N., Schnitzler, C. E., Chung, S., Robinson, J., Gerard, N. P., Gerard, C., Choe, H., and Sodroski, J. (2000). A tyrosine-sulfated peptide based on the N terminus of CCR5 interacts with a CD4-enhanced epitope of the HIV-1 gp120 envelope glycoprotein and inhibits HIV-1 entry. Journal of Biological Chemistry 275, 33516-33521.

Fenn, J. B., Mann, M., Meng, C. K., Wong, S. F., and Whitehouse, C. M. (1989). Science 246, 64.

Fields, G. B., and Fields, C. G. (1991). Solvation Effects in Solid-Phase Peptide-Synthesis. Journal of the American Chemical Society 113, 4202-4207.

Fields, G. B., and Noble, R. L. (1990). Solid-Phase Peptide-Synthesis Utilizing 9-Fluorenylmethoxycarbonyl Amino-Acids. International Journal of Peptide and Protein Research 35.161-214.

Fields, G. B., Tian, Z., and Barany, G. (1992). In Synthetic Peptides. A User's Guide, G. A. Grant, ed. (New York: W. H. Freeman and Co.), pp. 77-183.

Fitzpatrick, L. J., and Rivero, R. A. (1997). Solid phase synthesis of substituted aminosulfonyl ureas using a sulfonylcarbamate linker. Tetrahedron Letters 38, 7479-7482.

Forsen, S. K. K. (1994). Calcium in biological systems, H. B. L. J.; I. G. Bertini, S. J.; Valentine, J. S., ed.: University Science Books: Mill Valley, Calif.).

Foxall, C., Watson, S. R., Dowbenko, D., Fennie, C., Lasky, L. A., Kiso, M., Hasegawa, A., Asa, D, and Brandley, B. K. (1992). The Three Members of the Selectin Receptor Family Recognize a Common Carbohydrate Epitope, the Sialyl Lewis" Oligosaccharide. J. Cell Biol. 117, 895-902.

Fujii, N., Futaki, S., Funakoshi, S., Akaji, K., Morimoto, H., Doi, R., Inoue, K., Kogire, M., Sumi, S., Yun, M., To be, T., Aono, M., Matsuda, M., Narusawa, H., Moriga, M., and Yajima, H. (1988). Studies On Peptides 160 Synthesis of a 33-Residue Peptide Corresponding to the Entire Amino-Acid Sequence of Human Cholecystokinin (HCCK-33). Chemical & Pharmaceutical Bulletin 36, 3281-3291.

Futaki, S., Taike, T., Akita, T., and Kitagawa, K. (1992). Syntheses of 2 Tyrosine Sulfate Containing Peptides, Leucosulfakinin (LSK)-II and Cholecystokinin (CCK)-12, Using the 0-Para-04ethylsulphinyl)Benzyl Serine For the Selective Sulfation of Tyrosine. Tetrahedron 48, 8899-8914.

Garcia Echeverria, C. (1995). Letters in Peptide Science 2, 93.

Garegg, P. J. (1997). Thioglycosides as glycosyl donors in oligosaccharide synthesis. In Advances in Carbohydrate Chemistry and Biochemistry, Vol 52, pp. 179-205.

Ge, M., Thompson, C., and Kahne, D. (1998). Reconstruction of vancomycin by chemical glycosylation of the pseudoaglycon. Journal of the American Chemical Society 120, 11014-1 1015.

Gibson, B. W. (1990). In Biological Mass Spectrometry, A. L. Burlingame and J. A. McCloskey, eds. (Amsterdam: Elsevier Science Publishers BV), pp. 315.

Gibson, B. W., Falick, A. M., Poulter, L., Williams, D. H., and Cohen, P. (1987). In Methods in Protein Sequence Analysis 1986, K. A. Walsh, ed. (Clifton, N.J.: Humana), pp. 463.

Gibson, F. S., Bergmeier, S. C., and Rapoport, H. (1994). Selective Removal of an N-Boc Protecting Group in the Presence of a Tert-Butyl Ester and Other Acid-Sensitive Groups. Journal of Organic Chemistry 59, 3216-3218.

Giuffre, L., Cordey, A.-S., Monai, N., Tardy, Y., and Schapira, M. (1997). Monocyte Adhesion to Activated Aortic Endothelium: Role of L-Selectin and Heparan Sulfate Proteoglycans. Journal of Cell Biology 136, 945-56.

Glover, N. R., and Tracey, A. S. (1999). Modeling studies of the interactions between the insulin receptor kinase domain and protein tyrosine phosphatase 1 B. Journal of the American Chemical Society 121, 3579-3589.

Golik, J., Dickey, J. K., Todderud, G., Lee, D., Alford, J., Huang, S., Klohr, S., Eustice, D., Aruffo, A., and Agler, M. L. (1996). Isolation and Structure Determination of Sulfonoquinovosyl Dipalmitoyl Glyceride, a P-Selectin Receptor Inhibitor from the Alga Dictyochloris fragrans. Journal of Natural Products 60, 387-9.

Gouilleux, L., Fehrentz, J. A., Winternitz, F., and Martinez, J. (1996). Solid phase synthesis of chiral 3-substituted quinazoline-2,4-diones. Tetrahedron Letters 37, 7031-7034.

Granert, C., Raud, J., Xie, X., Lindquist, L., and Lindbom, L. (1994). Inhibition of leukocyte rolling with polysaccharide fucoidin prevents pleocytosis in experimental meningitis in the rabbit. Journal of Clinical Investigation 93, 929-936.

Guibe, F. (1997). Allylic protecting groups and their use in a complete environment. 1. Allylic protection of alcohols. Tetrahedron 53, 13509-13556.

Guibe, F. (1998). Allylic protecting groups and their use in a complex environment—Part II: Allylic protecting groups and their removal through catalytic palladium pi-allyl methodology. Tetrahedron 54, 2967-3042.

Guillemin, J. C., Denis, J. M., Lasne, M. C., and Ripoll, J. L. (1988). Synthesis of Unstabilized Cyclic Imines By Vacuum Gas-Solid Reactions and Flash Vacuum Thermolysis. Tetrahedron 44, 4447-4455.

Guy, C. A., and Fields, G. B. (1997). Trifluoroacetic acid cleavage and deprotection of resin-bound peptides following synthesis by Fmoc chemistry. In Solid-Phase Peptide Synthesis, pp. 67-83.

Hagen, F. K., Hazes, B., Raffo, R., deSa, D., and Tabak, L. A. (1999). Structure-function analysis of the UDP-N-acetyl-D-galactosamine: Polypeptide N-acetylgalactosaminyltransferase—Essential residues lie in a predicted active site cleft resembling a lactose repressor fold. Journal of Biological Chemistry 274, 6797-6803.

Han, D. I., Kim, D. Y., and Oh, D. Y. (1989). Reaction of O,S-Acetals and Phosphites in the Presence of Lewis-Acids—Chemoselectivity in the Cleavage of the Acetals. Bulletin of the Korean Chemical Society 10, 329-330.

Han, Y. X., Bontems, S. L., Hegyes, P., Munson, M. C., Minor, C. A., Kates, S. A., Albericio, F., and Barany, G. (1996). Preparation and applications of xanthenylamide (XAL) handles for solid-phase synthesis of C-terminal peptide amides under particularly mild conditions. Journal of Organic Chemistry 61, 6326-6339.

Handa, A., Hoshino, H., Nakajima, K., Adachi, M., Ikeda, K., Achiwa, K., Itoh, T., and Suzuki, Y. (1991). Inhibition of Infection with Human Immunodeficiency Virus Type 1 by Sulfated Gangliosides. Biochemical and Biophysical Research Communications 175, 1-9.

Hanisch, F. G., Muller, S., Hassan, H., Clausen, H., Zachara, N., Gooley, A. A., Paulsen, H., Alving, K., and Peter-Katalinic, J. (1999). Dynamic epigenetic regulation of initial 0-glycosylation by UDP-N-acetylgalactosamine: peptide N-acetylgalactosaminyltransferases—Site-specific glycosylation of MUC1 repeat peptide influences the substrate qualities at adjacent or distant Ser/Thr positions. Journal of Biological Chemistry 274, 9946-9954.

Herdewijn, P., Claes, P. J., and Vanderhaeghe, H. (1982). Synthesis of Trans(+/−)6-Phenoxyacetamido-1-Methylene-3,3-Dicarboxymethyl-1-Carbapenam. Canadian Journal of Chemistry-Revue Canadienne De Chimie 60, 2903-2907.

Hickey, D. M. B., Mackenzie, A. R., Moody, C. J., and Rees, C. W. (1987). Vinyl Azides in Heterocyclic Synthesis 0.6. Synthesis of Isoquinolines By Intramolecular Aza-Wittig Reaction. Journal of the Chemical Society-Perkin Transactions 1, 921-926.

Hiltz, H., and Lipmann, F. (1955). The enzymatic activation of sulfate. Proceedings of the National Academy of Sciences of the United States of America 41, 880.

Hormozdiari, P., and Gani, D. (1996). Highly efficient solid-phase phosphopeptide synthesis using bis-(polyfluorophenyl) chlorophosphates: Preparation of serine-threonine protein phosphatase substrates. Tetrahedron Letters 37, 8227-8230.

Hortin, G., Folz, R., Gordon, J. I., and Strauss, A. W. (1986). Characterization of Sites of Tyrosine Sulfation in Proteins and Criteria For Predicting Their Occurrence. Biochemical and Biophysical Research Communications 141, 326-333.

Hortin, G. L., Farries, T. C., Graham, J. P., and Atkinson, J. P. (1989). Sulfation of Tyrosine Residues Increases Activity of the 4th Component of Complement. Proceedings of the National Academy of Sciences of the United States of America 86, 1338-1342.

Horuk, R., Hesselgesser, J., Zhou, Y. Q., Faulds, D., Halks-Miller, M., Harvey, S., Taub, D., Samson, M., Parrnentier, M., Rucker, J., Doranz, B. J., and Doms, R. W. (1998). The CC chemokine 1-309 inhibits CCR8-dependent infection by diverse HIV-1 strains. Journal of Biological Chemistry 273, 386-391.

Huttner, W. B., and Baeuerle, P. A. (1988). In Modem Cell Biology, B. Satir, ed. (New York: Alan R. Liss, Inc.), pp. 97-140.

Jarowicki, K., and Kocienski, P. (2000). Protecting groups. Journal of the Chemical Society-Perkin Transactions 1, 2495-2527.

Jensen, J. L., Maynard, D. F., Shaw, G. R., and Smith, T. W. (1992). Chemical-Reactions Mediated By Heavy-Metal Ions 0.2. Mercury Ligation Effects On the Hg(II)-Promoted Hydrolyzes of Benzaldehyde 0-Ethyl S-Ethyl and S-Phenyl Acetals. Journal of Organic Chemistry 57, 1982-1986.

Jobron, L., and Hindsgaul, O. (1999). Novel para-substituted benzyl ethers for hydroxyl group protection. Journal of the American Chemical Society 121, 5835-5836.

Johnson, R. C., Mayadas, T. N., Frenette, P. S., Mebius, R. E., Subramaniam, M., Lacasce, A., Hynes, R. O., and Wagner, D. D. (1995). Blood cell dynamics in P-selectin-deficient mice. Blood 86, 1106-1114.

Jones, G. A., Stirling, C. J. M., and Bromby, N. G. (1983). Elimination and Addition-Reactions 0.37. a Comparative-Study of Electronic, Steric, and Solvent Effects Upon Reactivity in Additions of Benzenesulfenyl Chloride to Alkenes. Journal of the Chemical Society-Perkin Transactions 2, 385-393.

Jones, J. (1994). The chemical synthesis of peptides (Oxford: Oxford University Press).

Kaiser, E. (1970). Analytical Biochemistry 34, 595.

Kansas, G. S. (1996). Selectins and their Ligands: Current Concepts and Controversies. Blood 88, 3259-87.

Kehoe, J. W., and Bertozzi, C. R. (2000). Tyrosine sulfation: a modulator of extracellular protein-protein interactions. Chemistry & Biology 7, 57-61.

Kenner, G. W., McDermott, J. R., and Sheppard, R. C. (1971). The safety catch principle in solid phase synthesis. Journal of the Chemical Society, Chemical Communications, 636-7.

Kerekgyarto, J., Agoston, K., Batta, G., Kamerling, J. P., and Vliegenthart, J. F. G. (1998). Synthesis of fully and partially benzylated glycosyl azides via thioalkyl glycosides as precursors for the preparation of N-glycopeptides. Tetrahedron Letters 39, 7189-7191.

Kice, J. L., and Anderson, J. M. (1966). Journal of the American Chemical Society 88, 5242-5245.

Kick, E. K., and Ellman, J. A. (1995). Expedient Method For the Solid-Phase Synthesis of Aspartic-Acid Protease Inhibitors Directed Toward the Generation of Libraries. Journal of Medicinal Chemistry 38, 1427-1430.

Kiessling, L. L. (2001). The periodic table of biology. Chemical 8c Engineering News 79, 246-246.

Kiessling, L. L., Young, T., and Mortell, K. H. (2001). Multivalency in Protein-Carbohydrate Recognition. In Glycoscience Chemistry and Chemical Biology, B. Fraser-Reid, K. Tatsuta and J. Thiem, eds. (Heidelberg: Springer), pp. 1817.

Kitagawa, K., Aida, C., Fujiwara, H., Yagami, T., and Futaki, S. (1997). Efficient solid-phase synthesis of sulfated tyrosine-containing peptides using 2-chlorotrityl resin: Facile synthesis of gastrin/cholecystokinin peptides. Tetrahedron Letters 38, 599-602.

Kitagawa, K., Aida, C., Fujiwara, H., Yagami, T., Futaki, S., Kogire, M., Ida, J., and Inoue, K. (2001). Facile solid-phase synthesis of sulfated tyrosine-containing peptides: Total synthesis of human big gastrin-II and cholecystokinin (CCK)-39(1,2). Journal of Organic Chemistry 66, 1-10.

Kitagawa, K., Futaki, S., and Yagami, T. (1994). A Novel-Approach for the Synthesis of Tyrosine Sulfate-Containing Peptides Using a Safety Catch Type Protecting Group as a Key Feature. Journal of Synthetic Organic Chemistry Japan 52, 675-685.

Kitas, E. (1994). International Journal of Peptide and Protein Research 43, 146.

Kitas, E. A., Knorr, R., Trzeciak, A., and Bannwarth, W. (1991). Alternative Strategies For the Fmoc Solid-Phase Synthesis of 0-4-Phospho-L-Tyrosine-Containing Peptides. Helvetica Chimica Acta 74, 1314-1328.

Kitas, E. A., Wade, J. D., Johns, R. B., Perich, J. W., and Tregear, G. W. (1991). Preparation and Use of N-Alpha-Fluorenylmethoxycarbonyl-0-Dibenzylphosphono-L-Tyrosine in Continuous-Flow Solid-Phase Peptide-Synthesis. Journal of the Chemical Society-Chemical Communications, 338-339.

Knorr, R., Trzeciak, A., Bannwarth, W., and Gillessen, D. (1989). New Coupling Reagents in Peptide Chemistry. Tetrahedron Letters 30, 1927-1930.

Koenig, A., Norgard-Sumnicht, K., Linhardt, R., and Varki, A. (1998). Differential Interactions of Heparin and Heparan Sulfate Glycosaminoglycans with the Selectins. Journal of Clinical Investigations 101, 877-89.

Kokotos, G., and Constantinou-Kokotou, V. (1992). Journal of Chemical Research 12, 3117-3132.

Konstantopoulos, K., and McIntire, L. V. (1996). Effects of Fluid Dynamic Forces on Vascular Cell Adhesion. Journal of Clinical Investigations 98, 2661-5.

Kurano, Y., Kimura, T., and Sakakibara, S. (1987). Total Synthesis of Porcine Cholecystokinin-33 (CCK-33). Journal of the Chemical Society-Chemical Communications, 323-325.

Kusutnoto, S., Sakai, K., and Shiba, T. (1986). 4-Azidobutyryl Group For Temporary Protection of Hydroxyl Functions. Bulletin of the Chemical Society of Japan 59, 1296-1298.

Lacombe, J. M., Andriamanampisoa, F., and Pavia, A. A. (1990). Solid-Phase Synthesis of Peptides Containing Phosphoserine Using Phosphate tert-Butyl Protecting Group. International Journal of Peptide and Protein Research 36, 275-280.

Larsson, E., and Luning, B. (1994). Solid-Phase Phosphorylation of a Peptide By the H-Phosphonate Method. Tetrahedron Letters 35, 2737-2738.

Lasky, L. A. (1995). Selectin-Carbohydrate Interactions and the Initiation of the Inflammatory Response. Annual Reviews in Biochemistry 64, 113-39.

Lasky, L. A. (1992). Selectins: Interpreters of Cell-Specific Carbohydrate Information During Inflammation. Science 258, 964-969.

Laudanna, C., Constantin, G., Baron, P., Scarpini, E., Scarlato, G., Cabrini, G., Dechecchi, C., Rossi, F., Cassatella, M. A., and Berton, G. (1995). Sulfatides Trigger Increase of Cytosolic Free Calcium and Enhanced Expression of Tumor Necrosis Factor-u and Interleukin-8 mRNA in Human Neutrophils. J. Biol. Chem. 269, 4021-4026.

Lawrence, M. B., and Springer, T. A. (1991). Leukocytes roll on a selectin at physiologic flow rates: Distinction from and prerequisite for adhesion through integrins. Cell 65, 859-873.

Leppanen, A., Mehta, P., Ouyang, Y. B., Ju, T. Z., Helin, J., Moore, K. L., van Die, I., Canfield, W. M., McEver, R. P., and Cummings, R. D. (1999). A novel glycosulfopeptide binds to P-selectin and inhibits leukocyte adhesion to P-selectin. Journal of Biological Chemistry 274, 24838-24848.

Leppanen, A., White, S. P., Helin, J., McEver, R. P., and Cummings, R. D. (2000). Binding of glycosulfopeptides to P-selectin requires stereospecific contributions of individual tyrosine sulfate and sugar residues. Journal of Biological Chemistry 275, 39569-39578.

Ley, K., Linnemann, G., Meinen, M., Stoolman, L. M., and Gaehtgens, P. (1993). Fucoidin, but not yeast polyphosphomannan PPME, inhibits leukocyte rolling in venules of the rat mesentery. Blood 81, 177-185.

Leyte, A., Vanschijndel, H. B., Niehrs, C., Huttner, W. B., Verbeet, M. P., Mertens, K., and Vanmourik, J. A. (1991). Sulfation of Tyr68 of Human Blood-Coagulation Factor-VIII Is Essential For the Interaction of Factor-VIII With Von-Willebrand Factor. Journal of Biological Chemistry 266, 740-746.

Li, F. G., Erickson, H. P., James, J. A., Moore, K. L., Cummings, R. D., and McEver, R. P. (1996). Visualization of P-selectin glycoprotein ligand-1 as a highly extended molecule and mapping of protein epitopes for monoclonal antibodies. Journal of Biological Chemistry 271, 6342-6348.

Liotta, A. S., Kole, H. K., Fales, H. M., Roth, J., and Bernier, M. (1994). A Synthetic Tris-Sulfotyrosyl Dodecapeptide Analog of the Insulin-Receptor 1146-Kinase Domain Inhibits Tyrosine Dephosphorylation of the Insulin-Receptor In-Situ. Journal of Biological Chemistry 269, 22996-23001.

Liu, S. F., Dockendorff, C., and Taylor, S. D. (2001). Synthesis of protected L-4-[sulfono(difluoromethyl)]phenylalanine and its incorporation into a peptide. Organic Letters 3, 1571-1574.

Liu, W., Ramachandran, V., Kang, J., Kishimoto, T. K., Cummings, R. D., and McEver, R. P. (1998). Identification of N-terminal residues on P-selectin glycoprotein ligand-1 required for binding to P-selectin. Journal of Biological Chemistry 273, 7078-7087.

Lorant, D. E., Topham, M. K., Whatley, R. E., McEver, R. P., McIntyre, T. M., Prescott, S. M., and Zimmerman, G. A. (1993). Inflammatory roles of P-selectin. Journal of Clinical Investigation 92, 559-570.

Loubinoux, B., and Gerardin, P. (1991). Protection of Acids by Abz Groups—Use in Peptide-Synthesis. Tetrahedron 47, 239-248.

Loubinoux, B., Miazimbakana, J., and Gerardin, P. (1989). Reactivity of New Precursors of Quinone Methides. Tetrahedron Letters 30, 1939-1942.

Loubinoux, B., Tabbache, S., Gerardin, P., and Miazimbakana, J. (1988). Protection of Phenols Via the Azidomethylene Group—Application in the Synthesis of Unstable Phenolic-Compounds. Tetrahedron 44, 6055-6064.

Lowe, J. B., and Ward, P. A. (1997). Therapeutic inhibition of carbohydrate-protein interactions in vivo. Journal of Clinical Investigation 99, 822-826.

Lu, Q. B., and Benneche, T. (1996). Synthesis of alpha-fluoro ethers by cleavage of O,S-acetals with xenon difluoride. Acta Chemica Scandinavica 50, 850-852.

Malhotra, R., Taylor, N. R., and Bird, M. I. (1996). Anionic phospholipids bind to L-selectin (but not E-selectin) at a site distinct from the carbohydrate-binding site. Biochemical Journal 314, 297-303.

Manning, D. D., Hu, X., Beck, P. J., and Kiessling, L. L. (1997). Synthesis of Sulfated Neoglycopolymers: Selective P-Selectin Inhibitors. J. Am. Chem. Soc. 119, 3161-2.

Marchese, P., Murata, M., Mazzucato, M., Pradella, P., Demarco, L., Ware, J., and Ruggeri, Z. M. (1995). Identification of 3 Tyrosine Residues of Glycoprotein Ib-Alpha With Distinct Roles in Von-Willebrand-Factor and Alpha-Thrombin Binding. Journal of Biological Chemistry 270, 9571-9578.

Marseigne, I., Roy, P., Dor, A., Durieux, C., Pelaprat, D., Reibaud, M., Blanchard, J. C., and Roques, B. P. (1989). Full Agonists of CckS Containing a Nonhydrolyzable Sulfated Tyrosine Residue. Journal of Medicinal Chemistry 32, 445-449.

Matsubayashi, Y., Hanai, H., Hara, O., and Sakagami, Y. (1996). Active fragments and analogs of the plant growth factor, phytosulfokine: Structure-activity relationships. Biochemical and Biophysical Research Communications 225, 209-214.

Mayadas, T. N., Johnson, R. C., Rayburn, H., Hynes, R. O., and Wagner, D. D. (1993). Leukocyte rolling and extravastion are severely compromised in P-selectin-deficient mice. Cell 74, 541-554.

McEver, R. P. (1998). Leukocyte adhesion through selectins under flow. Immunologist 6, 61-67.

McEver, R. P. (1997). Selectin-carbohydrate interactions during inflammation and metastasis. Glycoconjugate Journal 14, 585-591.

McEver, R. P., and Cummings, R. D. (1997). Role of PSGL-1 binding to selectins in leukocyte recruitment. Journal of Clinical Investigation 100, S97-S 103.

Mehta, P., Cummings, R. D., and McEver, R. P. (1998). Affinity and kinetic analysis of P-selectin binding to P-selectin glycoprotein ligand-1. Journal of Biological Chemistry 273, 32506-32513.

Merrifield, R. B. (1963). Solid Phase peptide Synthesis I. The synthesis of a Tetrapeptide. Journal of the American Chemical Society 85, 7129-7133.

Miller, S.C., and Scanlan, T. S. (1998). oNBS-SPPS: A new method for solid-phase peptide synthesis. Journal of the American Chemical Society 120, 2690-2691.

Mondor, I., Ugolini, S., and Sattentau, Q. J. (1998). Human immunodeficiency virus type 1 attachment to HeLa CD4 cells is CD4 independent and gp 120 dependent and requires cell surface heparans. Journal of Virology 72, 3623-3634.

Moore, K. L., Patel, K. D., Bruehl, R. E., Li, F. G., Johnson, D. A., Lichenstein, H. S., Cummings, R. D., Bainton, D. F., and McEver, R. P. (1995). P-Selectin Glycoprotein Ligand-1 Mediates Rolling of Human Neutrophils on P-Selectin. Journal of Cell Biology 128, 661-671.

Mulligan, M. S., Miyasaka, M., Suzuki, M., Kawashima, H., Iizuka, M., Hasegawa, A., Kiso, M., Warner, R. L., and Ward, P. A. (1995). Anti-inflammatory effects of sulfatides in selectin-dependent acute lung injury. International Immunology 7, 1107-13.

Nelson, R. M., Dolich, S., Aruffo, A., Cecconi, O., and Bevilacqua, M. P. (1993). Higher-Affinity Oligosaccharide Ligands for E-Selectin. J. Clin. Invest. 9I, 1157-1166.

Nicolaou, K. C., Chucholowski, A., Dolle, R. E., and Randall, J. L. (1984). Reactions of Glycosyl Fluorides—Synthesis of O-Glycosides, S-Glycosides, and N-Glycosides. Journal of the Chemical Society-Chemical Communications, 1155-1156.

Niehrs, C., Beisswanger, R., and Huttner, W. B. (1994). Protein-Tyrosine Sulfation, 1993—an Update. Chemico-Biological Interactions 92, 257-271.

Niehrs, C., Kraft, M., Lee, R. W. H., and Huttner, W. B. (1990). Analysis of the Substrate-Specificity of Tyrosylprotein Sulfotransferase Using Synthetic Peptides. Journal of Biological Chemistry 265, 8525-8532.

Norgard, K. E., Moore, K. L., Diaz, S., Stults, N. L., Ushiyama, S., McEver, R. P., Cummings, R. D., and Varki, A. (1993). Characterization of a Specific Ligand For P-Selectin On Myeloid Cells—a Minor Glycoprotein With Sialylated O-Linked Oligosaccharides. Journal of Biological Chemistry 268, 12764-12774.

Norgard-Surnnicht, K., and Varki, A. (1995). Endothelial heparan sulfate proteoglycans that bind to L-selectin have glucosamine residues with unsubstituted amino groups. Journal of Biological Chemistry 270, 12012-12024.

Okada, Y. (2001). Synthesis of peptides by solution methods. Current Organic Chemistry 5, 1-43.

Ottinger, E. A. (1996). Peptide Research 9, 223.

Ottinger, E. A., Shekels, L. L., Bernlohr, D. A., and Barany, G. (1993). Synthesis of Phosphotyrosine-Containing Peptides and Their Use As Substrates For Protein-Tyrosine Phosphatases. Biochemistry 32, 4354-4361.

Otvos, L., Elekes, I., and Lee, V. M. Y. (1989). Solid-Phase Synthesis of Phosphopeptides. International Journal of Peptide and Protein Research 34, 129-133.

Ouyang, Y. B., Lane, W. S., and Moore, K. L. (1998). Tyrosylprotein sulfotransferase: Purification and molecular cloning of an enzyme that catalyzes tyrosine O-sulfation, a common posttranslational modification of eukaryotic proteins. Proceedings of the National Academy of Sciences of the United States of America 95, 2896-2901.

Paabo, S. (2001). Genomics and society—The human genome and our view of ourselves. Science 291, 1219.

Paladino, J., Guyard, C., Thurieau, C., and Fauchere, J. L. (1993). Enantioselective Synthesis of (2S)-2-Amino-3-(4-Hydroxy-3-Phosphonophenyl)Propionic Acid (=3'-Phosphono-L-Tyrosine) and Its Incorporation Into Peptides. Helvetica Chimica Acta 76, 2465-2472.

Patai, S. (1990). The chemistry of sulphenic acids and their derivatives (Chichester: John Wiley and Sons, Ltd.).

Patankar, M. S., Oehninger, S., Barnett, T., Williams, R. L., and Clark, G. F. (1993). A revised structure for fucoidan may explain some of its biological activities. Journal of Biological Chemistry 268, 21770-21776.

Peltonen, L., and McKusick, V. A. (2001). Genomics and medicine—Dissecting human disease in the postgenomic era. Science 291, 1224.

Penke, B., and Rivier, J. (1987). Solid-Phase Synthesis of Peptide Amides On a Polystyrene Support Using Fluorenylmethoxycarbonyl Protecting Groups. Journal of Organic Chemistry 52, 1197-1200.

Perich, J. W. (1991). Synthesis of 0-Phosphoserine-Containing and 0-Phosphothreonine-Containing Peptides. Methods in Enzymology 201, 225-233.

Perich, J. W. (1991). Synthesis of 0-Phosphotyrosine-Containing Peptides. Methods in Enzymology 201, 234-245.

Perich, J. W. (1997). Synthesis of phosphopeptides using modem chemical approaches. In Solid-Phase Peptide Synthesis, Methods in Enzymology 289, pp. 245-266.

Perich, J. W., and Johns, R. B. (1988). Australian Journal of Chemistry 43, 1623.

Perich, J. W., and Johns, R. B. (1988). Di-Tert-Butyl N,N-Diethylphosphoramidite and Dibenzyl N,N-Diethylphosphoramidite—Highly Reactive Reagents For the Phosphite-Triester Phosphorylation of Serine-Containing Peptides. Tetrahedron Letters 29, 2369-2372.

Perich, J. W., Nguyen, D. L., and Reynolds, E. C. (1991). The Facile Synthesis of Ala-Glu-Tyr(P)-Ser-Ala By Global Di-Tert-Butyl N,N-Diethylphosphoramidite Phosphite-Triester Phosphorylation of a Resin-Bound Peptide. Tetrahedron Letters 32, 4033-4034.

Perich, J. W., and Reynolds, E. C. (1991). Fmoc Solid-Phase Synthesis of Tyr(P)-Containing Peptides Through Tert-Butyl Phosphate Protection. International Journal of Peptide and Protein Research 37, 572-575.

Pittman, D. D., Wang, J. H., and Kaufinan, R. J. (1992). Identification and Functional Importance of Tyrosine Sulfate Residues Within Recombinant Factor-VIII. Biochemistry 31, 33 15-3325.

Plante, O. J., Buchwald, S. L., and Seeberger, P. H. (2000). Halobenzyl ethers as protecting groups for organic synthesis. Journal of the American Chemical Society 122, 7148-7149.

Polley, M. J., Phillips, M. L., Wayner, E., Nudelman, E., Singhal, A. K., Hakamori, S.-I., and Paulson, J. C. (1991). CD62 and Endothelial Cell-Leukocyte Adhesion Molecule 1 (ELAM-1) Recognize the Same Carbohydrate Ligand, Sialyl-Lewis X. Proceedings of the National Academy of Sciences, USA 88, 6224-6228.

Pouyani, T., and Seed, B. (1995). PSGL-1 Recognition of P-Selectin Is Controlled By a Tyrosine Sulfation Consensus At the PSGL-1 Amino-Terminus. Cell 83, 333-343.

Raju, B., and Kogan, T. P. (1997). Solid phase synthesis of sulfonamides using a carbamate linker. Tetrahedron Letters 38, 3373-3376.

Ramachandran, V., Nollert, M. U., Qiu, H. Y., Liu, W. J., Cummings, R. D., Zhu, C., and McEver, R. P. (1999). Tyrosine replacement in P-selectin glycoprotein ligand-1 affects distinct kinetic and mechanical properties of bonds with P- and L-selectin. Proceedings of the National Academy of Sciences of the United States of America 96, 13771-13776.

Rensdomiano, S., Hortin, G. L., and Roth, J. A. (1989). Sulfation of Tert-Butoxycarbonylcholecystokinin and Other Peptides By Rat-Liver Tyrosylprotein Sulfotransferase. Molecular Pharmacology 36, 647-653.

Ripka, W. C. (2000). Ann. Rep. Med. Chem. 35, 231-250.

Roderiquez, G., Oravecz, T., Yanagishita, M., Bouhabib, D. C., Mostowski, H., and Norcross, M. A. (1995). Mediation of Human-Immunodeficiency-Virus Type-1 Binding By Interaction of Cell-Surface Heparan-Sulfate Proteoglycans IVith the V3 Region of Envelope Gp120-Gp41. Journal of Virology 69, 2233-2239.

Rosenquist, G. L., and Nicholas, H. B. (1993). Analysis of Sequence Requirements For Protein Tyrosine Sulfation. Protein Science 2, 215-222.

Sakaitani, M., and Ohfine, Y. (1985). Selective Transformation of N-Tert-Butoxycarbonyl Group Into N-Alkoxy-Carbonyl Group Via N-Carboxylate Ion Equivalent. Tetrahedron Letters 26, 5543-5546.

Sako, D., Chang, X. J., Barone, K. M., Vachino, G., White, H. M., Shaw, G., Veldman, G. M., Bean, K. M., Ahern, T. J., Furie, B., Cumming, D. A., and Larsen, G. R. (1993).

Expression Cloning of a Functional Glycoprotein Ligand For P-Selectin. Cell 75, 1179-1186.

Sako, D., Comess, K. M., Barone, K. M., Camphausen, R. T.; Cumming, D. A., and Shaw, G. D. (1995). A Sulfated Peptide Segment at the Amino-Terminus of PSGL-1 Is Critical for P-Selectin Binding. Cell 83, 323-331.

Scriven, E. F. V., and Turnbull, K. (1988). Azides—Their Preparation and Synthetic Uses. Chemical Reviews 88, 297-368.

Shimonishi, Y., Sakakibara, S., and Akabori, S. (1962). Bulletin of the Chemical Society of Japan. 35, 1966-1970.

Skrzypczakjankun, E., Carperos, V., Bourdon, P., Fenton, J. W., Maraganore, J. M., and Tulinsky, A. (1991). X-Ray Crystallographic Structures of the Hirugen-Thrombin and Hirulog-Thrombin Complexes At 2.2 A Resolution. Thrombosis and Haemostasis 65, 830-830.

Skrzypczakjankun, E., Carperos, V. E., Ravichandran, K. G., Tulinsky, A., Westbrook, M., and Maraganore. J. M. (1991). Structure of the Hirugen and Hirulog-1 Complexes of Alpha-Thrombin. Journal of Molecular Biology 221, 1379-1393.

Sole, N. A., Han, Y., Vagner, J., Gross, C. M., Tejbrant, J., and Barany, G. (1996). In Peptides-Chemistry, Structure and Biology: Proceedings of the Fourteenth American Peptide Symposium, P. T. P. Kaumaya and R. S. Hodges, eds. (Kingswinford, England: Mayflower Scientific Ltd.), pp. 113-114.

Soli, E. D., and DeShong, P. (1999). Advances in glycosyl azide preparation via hypervalent silicates. Journal of Organic Chemistry 64, 9724-9726.

Soli, E. D., Manoso, A. S., Patterson, M. C., DeShong, P., Favor, D. A., Hirschmann, R., and Smith, A. B. (1999). Azide and cyanide displacements via hypervalent silicate intermediates. Journal of Organic Chemistry 64, 3171-3177.

Somers, W. S., Tang, J., Shaw, G. D., and Carnphausen, R. T. (2000). Insights into the molecular basis of leukocyte tethering and rolling revealed by structures of P- and E-selectin bound to SLe(X) and PSGL-1. Cell 103, 467-479.

Spevak, W., Foxall, C., Charych, D. H., Dasgupta, F., and Nagy, J. O. (1996). Carbohydrates in an Acidic Multivalent Assembly—Nanomolar P-selectin INhibitors. Journal of Medicinal Chemistry 39, 1018-20.

Springer, T. A. (1994). Traffic Signals for Lymphocyte Recirculation and Leukocyte Emigration: The Multistep Paradigm. Cell 76, 301-314.

Springer, T. A. (1995). Traffic Signals on Endothelium for Lymphocyte Recirculation and Leukocyte Emigration. Annual Review of Physiology 57, 827-872.

Stewart, J. M. (1981). In The Peptides, E. Gross and J. Meienhofer, eds. (London: Academic Press), pp. Chapter 4.

Stewart, J. M. (1997). Cleavage methods following Boc-based solid-phase peptide synthesis. In Solid-Phase Peptide Synthesis, Methods in Enzymology 289, pp. 29-44.

Stone, S. R., and Hofsteenge, J. (1986). Kinetics of the inhibition of thrombin by hirudin. Biochemistry 25, 4622-4628.

Stoolman, L. M., Tenforde, T. S., and Rosen, S. D. (1984). Phoshomannosyl receptors may participate in the adhesive interaction between lymphocytes and high endothelial venules. Journal of Cell Biology 99, 1535-1540.

Tatewaki, M., Yamaguchi, K., Matsuoka, M., Ishii, T., Miyasaka, M., Mori, S., Takatsuki, K., and Watanabe, T. (1995). Constitutive Overexpression of the L-selectin Gene in Fresh Leukemic Cells of Adult T-Cell Leukemia that can be Transactivated by Human T-Cell Lymphotropic Virus Type 1 Tax. Blood 86, 3109-17.

Tedder, T. F., Steeber, D. A., and Pizcueta, P. (1995). L-Selectin—deficient Mice Have Impaired Leukocyte Recruitment into Inflammatory Sites: Journal of Experimental-Medicine 181, 2259-64.

Tegge, T. (1994). International Journal of Peptide and Protein Research 43, 448.

Theodoridis, G. (2000). Nitrogen protecting groups: Recent developments and new applications. Tetrahedron 56, 2339-2358.

Unsworth, C. D., Hughes, J., and Morley, J. S. (1982). O-Sulfated Leu-Enkephalin in Brain. Nature 295, 519-522.

Unverzagt, C., and Kunz, H. (1992). Stereoselective Synthesis of Glycosides and Anomeric Azides of Glucosamine. Journal Fur Praktische Chemie-Chemiker-Zeitung 334, 570-578.

Vachino, G., Chang, X. J., Veldman, G. M., Kumar, R., Sako, D., Fouser, L. A., Berndt, M. C., and Cumming, D. A. (1995). P-Selectin Glycoprotein Ligand-1 Is the Major Counter-Receptor for P-Selectin on Stimulated T-Cells and Is Widely Distributed in Nonfunctional Form on Many Lyrnphocytic Cells. Journal of Biological Chemistry 270, 21966-21974.

Valerio, R. M., Perich, J. W., Kitas, E. A., Alewood, P. F., and Johns, R. B. (1989). Synthesis of 0-Phosphotyrosine-Containing Peptides 0.2. Solution-Phase Synthesis of Asn-Glu-Ptyr-Thr-Ala Through Methyl Phosphate Protection. Australian Journal of Chemistry 42, 1519-1525.

Varki, A. (1994). Selectin ligands. Proc. Natl. Acad. Sci. 91, 7390-7397.

Vedejs, E., Lin, S. Z., Klapars, A., and Wang, J. B. (1996). Heteroarene-2-sulfonyl chlorides (BtsC1; ThsC1): Reagents for nitrogen protection and >99% racemization-free phenylglycine activation with SOC12. Journal of the American Chemical Society 118, 9796-9797.

Venter, J. C., Adams, M. D., Myers, E. W., Li, P. W., Mural, R. J., Sutton, G. G., Smith, H. O., Yandell, M., Evans, C. A., Holt, R. A., Gocayne, J. D., Arnanatides, P., Ballew, R. M., Huson, D. H., Wortman, J. R., Zhang, Q., Kodira, C. D., Zheng, X. Q. H., Chen, L., Skupski, M., Subramanian, G., Thomas, P. D., Zhang, J. H., Miklos, G. L. G., Nelson, C., Broder, S., Clark, A. G., Nadeau, C., McKusick, V. A., Zinder, N., Levine, A. J., Roberts, R. J., Simon, M., Slayman, C., Hunkapiller, M., Bolanos, R., Delcher, A., Dew, I., Fasulo, D., Flanigan, M., Florea, L., Halpern, A., Hannenhalli, S., Kravitz, S., Levy, S., Mobarry, C., Reinert, K., Remington, K., Abu-Threideh, J., Beasley, E., Biddick, K., Bonazzi, V., Brandon, R., Cargill, M., Chandramouliswaran, I., Charlab, R., Chaturvedi, K., Deng, Z. M., Di Francesco, V., Dunn, P., Eilbeck, K., Evangelista, C., Gabrielian, A. E., Gan, W., Ge, W. M., Gong, F. C., Gu, Z. P., Guan, P., Heiman, T. J., Higgins, M. E., Ji, R. R., Ke, Z. X., Ketchum, K. A., Lai, Z. W., Lei, Y. D., Li, Z. Y., Li, J. Y., Liang, Y., Lin, X. Y., Lu, F., Merkulov, G. V., lylilshina, N., Moore, H. M., Naik, A. K., Narayan, V. A., Neelam, B., Nusskern, D., Rusch, D. B., Salzberg, S., Shao, W., Shue, B. X., Sun, J. T., Wang, Z. Y., Wang, A. H., Wang, X., Wang, J., Wei, M. H., Wides, R., Xiao, C. L., Yan, C. H., et al. (2001). The sequence of the human genome. Science 291, 1304.

Wakamiya, T., Saruta, K., Yasuoka, J., and Kusumoto, S. (1994). An Efficient Procedure For Solid-Phase Synthesis of Phosphopeptides By the Fmoc Strategy. Chemistry Letters, 1099-1102.

Weston, S. A., and Parish, C. R. (1991). Modification of lymphocyte migration by mannans and phoshomannans. Journal of Immunology 146, 4180-4186.

White, P., and Beythien, J. (1996). In Innovations & Perspectives in Solid Phase Synthesis & Combinatorial Libraries, 4th International Symposium, R. Epton, ed. (Birmingham: Mayflower Scientific Ltd.), pp. 557.

Whyte, A., Wooding, P., Nayeem, N., Watson, S. R., Rosen, S. D., and Binns, R. M. (1995). The L-selectin counter-receptor in porcine lymph nodes. Biochemical Society Transactions 23, 159.

Wilkins, P. P., McEver, R. P., and Cummings, R. D. (1996). Characterization of the 0-glycans of PSGL-1 from HL-60 cells. Faseb Journal 10, 1321-1321.

Wilkins, P. P., McEver, R. P., and Cummings, R. D. (1996). Structures of the 0-glycans on P-selectin glycoprotein ligand-I from HL-60 cells. Journal of Biological Chemistry 271, 18732-18742.

Wilkins, P. P., Moore, K. L., McEver, R. P., and Cummings, R. D. (1995). Tyrosine Sulfation of P-Selectin Glycoprotein Ligand-1 Is Required for High-Affinity Binding to P-Selectin. Journal of Biological Chemistry 270, 22677-22680.

Wilson, L., and Bandurski, R. S. (1956). The Mechanism of "active sulfate" formation. Journal of the American Chemical Society 78, 6408.

Yagami, T., Kitagawa, K., and Futaki, S. (1995). Analysis of Sulfated Tyrosine-Containing Peptides By Liquid Secondary-Ion Mass-Spectrometry With Constant Neutral-Loss (80 Amu) Scanning. Analytical Sciences 11, 1025-1028.

Yagami, T., Kitagawa, K., and Futaki, S. (1995). Liquid Secondary-Ion Mass-Spectrometry of Peptides Containing Multiple Tyrosine-0-Sulfates. Rapid Communications in Mass Spectrometry 9, 1335-1341.

Ye, B., Akamatsu, M., Shoelson, S. E., Wolf, G., Giorgettiperaldi, S., Yan, X. J., Roller, P. P., and Burke, T. R. (1995). L-0-(2-Malonyl)Tyrosine—a New Phosphotyrosyl Mimetic For the Preparation of Src-Homology-2 Domain Inhibitory Peptides. Journal of Medicinal Chemistry 38, 4270-4275.

Yon, M. (1994). In Innovations and Perspectives in Solid Phase Synthesis, 1993: Biological and Biomedical Applications., R. Epton, ed. (Birmingham: Mayflower Worldwide Ltd.), pp. 707.

Zhang, A. J., Russell, D. H., Zhu, J. P., and Burgess, K. (1998). A method for removal of N-BOC protecting groups from substrates on TFA-sensitive resins. Tetrahedron Letters 39, 7439-7442.

Zimmerman, G. A., McIntyre, T. M., and Prescott, S. M. (1996). Adhesion and Signaling in Vascular Cell-Cell Interactions. Journal of Clinical Investigations 98, 1699-L 702.

Young, T. (2001) "A Strategy for the Synthesis of Sulfated Peptides" Ph.D. Thesis Univeristy of Wisconsin (Madison) Volume 62/07-B Dissertation Abstracts International.

Young, T.; Kiessling, L.L. "A Strategy for the Synthesis of Sulfated Peptides" (2002) Angewandte Chemie. Int. Ed. 41:3449-3451.

Each reference cited herein is incorporated by reference herein in its entirety. References cited herein and incorporated by reference herein are intended to provide art-known details concerning starting materials, reagents, solvents and reaction conditions for peptide synthesis, including soild phase peptide synthesis. References cited herein may also provide additional details of synthetic methods and analystical methods.

We claim:

1. A protected amino acid useful for synthesis of a selectively derivatized peptide which has the formula:

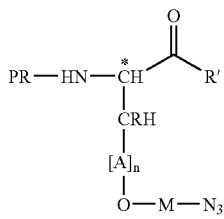

and salts thereof wherein:
* indicates that the indicated C may be chiral, non-racemic or racemic;
PR is any appropriate amine protecting group wherein the conditions for removal of the protecting group are substantially orthogonal to the conditions for removal of the azide-bearing protecting group;
R' is OH, OR, OAr, $NH_2$, NH(R or Ar), $NR_2$, $N(Ar)_2$, a group that generates an activated ester, a halogen, a substituted phenyl group, a halogenated phenyl group, benzotriazol-1-yl, N-hydroxysuccinimido, or 3,4-dihydro-4-oxo-1,2,3-benzotriazin-3-yl, where Ar is an optionally substituted aryl group, and where Ar is an aryl group other than an aryl group that contains an alkyl portion;
R is H or alkyl,
A is an optionally substituted phenyl group;
n is 0 or 1; and
M is selected from the group consisting of:
—$(CH_2)_m$— where m is 1-6;
—$CH_2$-phenyl- wherein the phenyl can be optionally substituted;
—$CH_2$-phenyl-O— wherein the phenyl can be optionally substituted;
—$(CR_2)_m$ where m is 1-6, each R selected independently of other R;
—CO—NH—$SO_2$—$CH_2$—$CH_2$—; and
—CO—NH—$CH_2$—$CH_2$—.

2. The protected amino acid of claim 1 wherein PR is acid labile.

3. The protected amino acid of claim 1 wherein PR is base labile.

4. The protected amino acid of claim 1 wherein PR is selected from the group consisting of Boc, Bpoc, Trityl, Fmoc, 2-nitrosulphonyl, dithiasuccinoyl, diphenylphosphinyl, and sulfonyl.

5. The protected amino acid of claim 1 wherein n is 1 and R is H.

6. The protected amino acid of claim 1 wherein n is 0 and R is $CH_3$.

7. The protected amino acid of claim 1 wherein n is 0 and R is H.

8. The protected amino acid of claim 1 wherein the amino-protecting group is Fmoc.

9. The protected amino acid of claim 8 wherein n is 1 and R is H.

10. The protected amino acid of claim 9 wherein M is —$CH_2$—.

11. The protected amino acid of claim 1 wherein M is —$CH_2$—.

12. The protected amino acid of claim 1 wherein R' is fluoride or chloride.

13. A kit for the synthesis of a derivatized peptide which comprises one or more of the azide-protected amino acids of claim 1.

14. The kit of claim 13 wherein, in the azide-protected amino acid, PR is acid labile.

15. The kit of claim 13 wherein, in the azide-protected amino acid, PR is base labile.

16. The kit of claim 13 wherein, in the azide-protected amino acid, PR is selected from the group consisting of Boc, Bpoc, Trityl, Fmoc, 2-nitrosulphonyl, dithiasuccinoyl, diphenylphosphinyl, and sulfonyl.

17. The kit of claim 13 wherein, in the azide protected amino acid, n is 1 and R is H.

18. The kit of claim 13 wherein, in the azide protected amino acid, n is 0 and R is $CH_3$.

19. The kit of claim 13 wherein, in the azide protected amino acid, n is 0 and R is H.

20. The kit of claim 13 wherein, in the azide protected amino acid, the amino-protecting group is Fmoc.

21. The kit of claim 20 wherein, in the azide protected amino acid, n is 1 and R is H.

22. The kit of claim 21 wherein, in the azide protected amino acid, M is —$CH_2$—.

23. The kit of claim 13 wherein, in the azide protected amino acid, M is —$CH_2$—.

24. The kit of claim 13 further comprising one or more amino acids for peptide synthesis other than azide-protected hydroxy amino acids wherein said one or more amino acids for peptide synthesis comprise α-amine group protection, optional side-chain protection and optional carboxy group protection, activation or both as appropriate for use with PR and the azide protecting group of the azide-protected hydroxy amino acids in the kit.

25. The kit of claim 24 wherein, in the azide-protected amino acid, PR is Fmoc.

26. The kit of claim 24 wherein, in the azide-protected amino acid, PR is Boc.

27. The kit of claim 13 further comprising solid support materials appropriate for conducting peptide synthesis employing the protected amino acid or acids provided in the kit.

28. The kit of claim 13 further comprising one or more reagents for deprotecting the azide-protected amino acids in the kit.

29. The kit of claim 13 further comprising one or more reagents for sulfation of a deprotected hydroxy amino acid.

30. The kit of claim 13 further comprising one or more reagents for phosphorylation of a deprotected hydroxy amino acid.

31. The kit of claim 13 further comprising one or more reagents for glycosylation of a deprotected hydroxy amino acid.

32. The kit of claim 13 further comprising instructions for conducting peptide synthesis employing the azide-protected amino acids in the kit.

33. A method for synthesizing a selectively modified peptide which comprises the step of synthesizing a selectively-modified peptide employing the kit of claim 13.

34. The method of claim 33 wherein at least a portion of the peptide is provided by step-wise solid phase peptide synthesis on a resin employing an amine-protected hydroxy amino acid in which the hydroxy group is protected with an azidomethylene group to incorporate at least one azide-protected hydroxy amino acid residue on a peptide synthesized on the resin.

35. The method of claim 34 wherein the amine protection group on the amine-protected hydroxy amino acid is an Fmoc group.

36. The method of claim 34 wherein the hydroxy amino acid is a tyrosine.

37. The method of claim 36 wherein the amine protection group on the amine-protected tyrosine is an Fmoc group.

38. The method of claim 34 wherein the azidomethylene protecting group is cleaved prior to cleavage of the peptide from the resin.

39. The method of claim 38 wherein the resin is a 2-chlorotrityl resin.

40. The protected amino acid of claim 1 wherein M is —$(CR_2)m$—.

41. The protected amino acid of claim 1 wherein M is —$(CH_2)m$—.

42. The protected amino acid of claim 9 wherein M is —$(CR_2)m$—.

43. The kit of claim 13 wherein, in the azide protected amino acid, M is —$CR_2)m$—.

44. The kit of claim 13 wherein, in the azide protected amino acid, M is —$CH_2)m$—.

45. The kit of claim 21 wherein, in the azide protected amino acid, M is —$CR_2)m$—.

46. The protected amino acid of claim 1 which is an L-isomer.

* * * * *